(12) United States Patent
Sternby

(10) Patent No.: US 11,992,589 B2
(45) Date of Patent: May 28, 2024

(54) MEASURING ACCESS FLOW RATE BY USE OF BLOOD TREATMENT MACHINE

(71) Applicant: GAMBRO LUNDIA AB, Lund (SE)

(72) Inventor: Jan Sternby, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 1372 days.

(21) Appl. No.: 16/338,658

(22) PCT Filed: Sep. 27, 2017

(86) PCT No.: PCT/EP2017/074516
§ 371 (c)(1),
(2) Date: Apr. 1, 2019

(87) PCT Pub. No.: WO2018/065275
PCT Pub. Date: Apr. 12, 2018

(65) Prior Publication Data
US 2020/0038572 A1    Feb. 6, 2020

(30) Foreign Application Priority Data

Oct. 3, 2016  (SE) .................................. 1651296-4

(51) Int. Cl.
*A61M 1/16*    (2006.01)
*A61M 1/36*    (2006.01)

(52) U.S. Cl.
CPC ........ *A61M 1/1615* (2014.02); *A61M 1/3604* (2014.02); *A61M 1/36225* (2022.05);
(Continued)

(58) Field of Classification Search
CPC .............. A61M 1/1615; A61M 1/3604; A61M 1/36225; A61M 1/3656; A61M 1/3658; A61M 1/362264
See application file for complete search history.

(56) References Cited

U.S. PATENT DOCUMENTS

| 5,024,756 A | 1/1991 | Sternby |
| 5,100,554 A | 3/1992 | Polaschegg |

(Continued)

FOREIGN PATENT DOCUMENTS

| EP | 1666078 | 2/1988 |
| EP | 0658352 | 6/1995 |

(Continued)

OTHER PUBLICATIONS

Sakiewicz et al., "Introduction of a Switch that Can Reverse Blood Flow Direction On-Line during Hemodialysis," ASAIO Journal 2000—XP-000935953—5 pages.

(Continued)

*Primary Examiner* — John Kim
(74) *Attorney, Agent, or Firm* — K&L Gates LLP

(57) ABSTRACT

A device for determining the access flow rate of a patient when connected to a blood treatment machine performs a measurement phase (40), in which the blood treatment machine is caused (41, 43) to operate in first and second operating states, wherein the second operating state at least differs from the first operating state by a change of flow direction of blood or treatment fluid through a dialyzer of the blood treatment machine. Based on sensor values representing a fluid property (42, 44) of the treatment fluid in the first and second operating states, the device computes (45) a measurement value of comparison parameter (e.g. a ratio or a difference) that compares treatment efficiency in the first operating state to treatment efficiency in the second operating state, and determines (46), based on the measurement value, an estimated value of the access flow rate.

25 Claims, 7 Drawing Sheets

(52) U.S. Cl.
CPC ........ *A61M 1/3656* (2014.02); *A61M 1/3658* (2014.02); *A61M 1/362264* (2022.05)

(56) References Cited

U.S. PATENT DOCUMENTS

| | | | |
|---|---|---|---|
| 5,312,550 | A | 5/1994 | Hester |
| 5,453,576 | A | 9/1995 | Krivitski |
| 5,510,716 | A | 4/1996 | Buffaloe, IV et al. |
| 5,510,717 | A | 4/1996 | Buffaloe, IV et al. |
| 5,567,320 | A | 10/1996 | Goux et al. |
| 5,595,182 | A | 1/1997 | Krivitski |
| 5,685,989 | A | 11/1997 | Krivitski et al. |
| 5,830,365 | A | 11/1998 | Schneditz |
| 6,648,845 | B1 | 11/2003 | Gotch et al. |
| 6,702,774 | B1 | 3/2004 | Polaschegg |
| 6,726,647 | B1 | 4/2004 | Sternby et al. |
| 6,746,407 | B2 | 6/2004 | Steuer et al. |
| 7,615,058 | B2 | 11/2009 | O'Mahony |
| 7,896,831 | B2 | 3/2011 | Sternby et al. |
| 2004/0168969 | A1* | 9/2004 | Sternby .......... A61M 1/16 604/4.01 |
| 2005/0082226 | A1* | 4/2005 | Bene .......... A61M 1/3656 210/96.2 |
| 2009/0017126 | A1 | 1/2009 | Sternby et al. |
| 2013/0193039 | A1 | 8/2013 | Kopperschmidt |
| 2013/0338560 | A1 | 12/2013 | Bene et al. |
| 2017/0372600 | A1 | 12/2017 | Palin et al. |
| 2019/0029630 | A1 | 1/2019 | Aschoff et al. |

FOREIGN PATENT DOCUMENTS

| | | |
|---|---|---|
| EP | 0658352 | 10/1997 |
| EP | 0928614 | 7/1999 |
| EP | 0928614 | 8/2005 |
| EP | 1938847 | 7/2008 |
| EP | 1666078 A2 | 10/2009 |
| EP | 1938847 | 11/2014 |
| WO | 02053212 | 7/2002 |
| WO | 2002053212 | 7/2002 |
| WO | 03066135 | 8/2003 |
| WO | 2003066135 | 8/2003 |

OTHER PUBLICATIONS

European Office Action dated Mar. 1, 2023—Appl. No. 17 777 020.3-1113, 10 pages.
International Search Report and Written Opinion for International Application No. PCT/EP2017/074516, dated Jan. 1, 2018; (14 pages).

* cited by examiner

MEASURING ACCESS FLOW RATE BY USE OF BLOOD TREATMENT MACHINE

PRIORITY CLAIM

The present application is a National Phase of International Application No. PCT/EP2017/074516, filed Sep. 27, 2017, which claims priority to Swedish Application No. 1651296-4, filed Oct. 3, 2016, the entire contents of each of which are incorporated herein by reference and relied upon.

TECHNICAL FIELD

The present invention relates to a technique for measurement of fluid flow rate in a vascular access of a patient when connected to a blood treatment machine.

BACKGROUND ART

There are several types of blood treatment machines that perform blood treatment by withdrawing blood from a human subject (patient), processing at least part of the blood and returning processed blood to the patient. Such blood treatment involves, for example, hemodialysis, hemofiltration, hemodiafiltration, plasmapheresis, blood component separation, blood oxygenation, etc. Normally, blood is withdrawn through an access device connected to a dedicated vascular access (blood vessel) on the patient and the processed blood is returned to the same or another access device connected to the same vascular access.

In hemodialysis and similar treatments, the vascular access is commonly surgically created in the nature of an arterio-venous (AV) shunt, commonly referred to as a fistula. The access devices are needles that are inserted in the fistula. Blood is taken out from the fistula via a needle in an upstream position (arterial needle) and blood is returned to the fistula via a needle at a downstream position (venous needle).

The AV shunt or fistula is a vascular access having capability of providing a high blood flow and being operative during several years and even tens of years. It is produced by operatively connecting, for example, the radial artery to the cephalic vein at the level of the forearm. The venous limb of the fistula thickens during the course of several months, permitting repeated insertion of dialysis needles.

An alternative vascular access is the arterio-venous (AV) graft, in which a connection is generated from, for example, the radial artery at the wrist to the basilic vein. The connection is made with a tube graft made from e.g. autogenous saphenous vein or from polytetrafluoroethylene (PTFE, Teflon). Access devices in the form of needles are inserted in the graft.

A further example of a vascular access is a silicon, dual-lumen catheter surgically implanted into one of the large veins.

Further types of vascular access find use in specific situations, like a no-needle AV graft consisting of a T-tube linked to a standard PTFE graft. The T-tube is implanted in the skin, and connection is obtained either by unscrewing a plastic plug or by puncturing a septum of said T-tube with a needle. Other methods and devices are also known.

During the above-mentioned blood treatment therapies, such as hemodialysis, it is desirable to withdraw, from the patient, a constant blood flow rate of 150-500 ml/min or even higher, and the vascular access needs to be prepared for delivering such flow rates. The blood flow in an AV fistula is often 800 ml/min or larger, permitting delivery of a blood flow rate in the desired range.

In the absence of a sufficient forward blood flow, the blood treatment machine will take up some of the already treated blood entering the fistula via the venous needle, so called access or fistula recirculation, leading to poor treatment results and progressive reduction of treatment efficiency.

A common cause of poor flow within AV fistulas is partial obstruction of the venous limb due to fibrosis secondary to multiple venipunctures. Moreover, stenosis causes a reduction of access flow.

It has been found that access flow rate often exhibits a long plateau time period with sufficient access flow, followed by a short period of a few weeks with markedly reduced access flow leading to recirculation and ultimately access failure. By constantly monitoring the evolution of the access flow during consecutive treatment sessions, it is possible to detect imminent access flow problems. Proper detection of access flow reduction may help in carrying out a maintenance procedure on the access thereby avoiding any access failure.

A non-invasive technique that allows measurement of flow through AV fistulas and grafts is color Doppler ultrasound. Magnetic Resonance Imaging (MRI) has also been used. However, these techniques require expensive equipment and are not easily used in the dialysis clinic environment.

Several methods have been suggested for monitoring recirculation and access flow. Many of these methods involve injection of a marker substance in blood, and the resultant recirculation is detected. The methods normally involve measurement of a property in the extracorporeal blood circuit. Examples of such methods can be found in U.S. Pat. Nos. 5,685,989, 5,595,182, 5,453,576, 5,510,716, 5,510,717, 5,312,550, etc. Such methods have the disadvantage that they require the injection of the marker substance and external equipment for the measurements.

Another technique relies on an intermittent flow reversal of the blood flow to and from the vascular access in connection with blood treatment machines that are configured to process the blood in a blood filter (dialyzer) by through-flow of blood and treatment fluid on opposite sides of a semi-permeable membrane. For example, U.S. Pat. Nos. 6,726,647, 7,896,831 and EP 1938847 propose to calculate the access flow rate by an algebraic equation involving measured values of either urea concentration or conductivity in the treatment fluid, for both a normal blood flow to the vascular access and a reversed blood flow. The algebraic equation also involves an estimated, measured or theoretically calculated value of the in-vivo clearance or dialysance (also known as effective clearance or dialysance) of the blood treatment machine. A variant is disclosed in EP0928614, in which the access flow rate is calculated by an algebraic equation involving measured values of the in-vivo clearance for both normal and reversed blood flow to the vascular access. In all of these techniques, the intermittent flow reversal may be achieved by a caretaker manually switching place of the needles in the vascular access. However, such manual intervention is complex, time-consuming and brings discomfort to the patient, and may also introduce significant errors to the calculated access flow rate. Instead, a switching device in the form a valve or a system of valves is provided in the blood transport system of the blood treatment machine to selectively reverse the blood flow through the access devices. Normally, the blood transport system includes a disposable (line set or cassette) with blood pathways, which is installed between the dialyzer and the access devices in engagement with a blood pump. The blood pump is operable to pump blood from one access device, through the dialyzer to the other access device. The switching device is proposed to be included in this disposable, which means that a dedicated disposable needs to be kept in stock at the clinic for installation in the blood treatment machine whenever the access flow rate should be measured. This provides logistic challenges and increases the cost of treatment.

Another drawback of the foregoing flow reversal techniques is the need to measure the in-vivo clearance with high accuracy. It is well-known in the art to determine the in-vivo clearance in a dialysis machine by generating a short-term bolus of a parameter of the treatment fluid (e.g. concentration or temperature) entering the dialyzer and by measuring this parameter at least downstream of the dialyzer, e.g. as disclosed in U.S. Pat. Nos. 5,024,756, 5,100,554, EP0658352 and U.S. Pat. No. 6,702,774. This "bolus technique" has its inherent drawbacks when implemented in a dialysis machine. During each bolus generation, the dialysis machine needs to have a preparation system for treatment fluid that is capable of producing an intermittent, short-term change of composition or temperature of the treatment fluid. Even if the machine has such a preparation system, the intermittent change may cause subsequent instabilities in the composition and/or temperature of the treatment fluid. Thus, the bolus technique may only be applicable to certain dialysis machines and may require advanced mechanisms for controlling its operation. Moreover, the bolus technique is relatively time-consuming, since even a short-term bolus results in a relatively long pulse downstream of the dialyzer, due to the exchange process in the dialyzer. It is also a challenge to determine the in-vivo clearance with sufficient accuracy for calculation of the access flow rate. Further, it is necessary to ensure that the bolus change in concentration or temperature of the treatment fluid lies within physiologically acceptable limits.

SUMMARY

It is an objective of the invention to at least partly overcome one or more of limitations of the prior art.

A further objective is to provide a technique for determining a fluid flow rate in a vascular access of a patient when connected to a blood treatment machine.

Another objective is to provide such a technique which is simple to implement and obviates the need to install a dedicated line set or cassette in the blood treatment machine.

Yet another objective is to provide such a technique that obviates the need to determine the in-vivo clearance of the blood treatment machine.

One or more of these objectives, as well as further objectives that may appear from the description below, are at least partly achieved by a control device, a blood treatment machine, a method and a computer-readable medium, embodiments thereof being defined by the dependent claims.

A first aspect of the invention is a device for determining a fluid flow rate in a vascular access of a patient when connected to a blood treatment machine that comprises an extracorporeal blood flow circuit and a treatment fluid flow circuit. The extracorporeal blood flow circuit comprises first and second access devices for connection to the vascular access and a blood pump operable to generate a flow of blood in the extracorporeal blood flow circuit from the first access device through a blood compartment of a dialyzer and to the second access device. The treatment fluid flow circuit is configured to generate a flow of treatment fluid through a treatment fluid compartment of the dialyzer, the treatment fluid compartment being separated from the blood compartment by a semi-permeable membrane. The device is configured to, during a measurement phase: cause the blood treatment machine to switch between a first operating state and a second operating state, wherein the second operating state at least differs from the first operating state by a change of flow direction of the blood or the treatment fluid through the dialyzer; acquire an output signal of at least one sensor in the blood treatment machine in the first and second operating states; compute, based on the output signal, a measurement value of a comparison parameter that compares treatment efficiency in the first operating state to treatment efficiency in the second operating state; and determine, based on the measurement value, an estimated value of the fluid flow rate in the vascular access.

The first aspect thus relies on switching the flow direction of blood or treatment fluid in the dialyzer, instead of or in addition to switching the flow direction of blood in relation to the vascular access. By proper implementation of the switching, the first aspect makes it possible to obviate the need to install a specialized line set or cassette in the blood treatment machine. As defined in more detail below, the switching may be implemented by a reversal of the blood pump, which results in a simultaneous reversal of the blood flow direction in the dialyzer and the blood flow direction in relation to the vascular access. Alternatively or additionally, the switching may be implemented by a flow switching device in the treatment fluid flow circuit. In both examples, the switching is simple to implement and requires no specialized line set or cassette to be installed in the blood treatment machine. Instead, the blood pump and the flow switching device may be permanently installed in the blood treatment machine, so the switching may be simply executed by generating a predefined control signal for the blood treatment machine. However, in an alternative, the device may be configured to cause the blood treatment machine to switch between the first operating state and the second operating state by prompting an operator to manually set the machine in the respective state, e.g. by manipulating the blood pump or the flow switching device.

The first aspect is based on the counterintuitive finding that the blood flow rate in the vascular access may be determined by monitoring a change of treatment efficiency caused, at least partly, by a change of flow direction distant from the vascular access. The first aspect is also based on the further finding that the estimated access flow rate may be conveniently obtained by measuring a comparison parameter that compares or relates the treatment efficiency in the first operating state to the treatment efficiency in the second operating state. By using such a comparison parameter it is possible to obtain a functional relation that scales sufficiently with access flow rate to give a reasonable accuracy of the estimated access flow rate. The measurement value of the comparison parameter may be computed as a function of a difference between the treatment efficiencies in the first and second operating states. Alternatively, the measurement value of the comparison parameter may be computed as a function of a ratio of the treatment efficiencies in the first and second operating states. The use of a ratio makes it possible to obviate the need to determine the treatment efficiency in terms of the in-vivo clearance of the blood treatment machine. Instead, it has been found that the respective treatment efficiency may be represented, in such a ratio, by a difference in a property of the treatment fluid between the inlet and outlet of the treatment fluid chamber in the dialyzer, as measured by the at least one sensor. Compared to the conventional bolus technique for measuring in-vivo clearance, the difference is obtained without generating a bolus in the measured property. Thus, the use of differences instead of in-vivo clearance will shorten the measurement time considerably. By shortening the time between measurements, the use of differences is also likely to improve the accuracy of the estimated access flow rate.

In the following, various embodiments of the first aspect are defined. These embodiments provide at least some of the technical effects and advantages described in the foregoing, as well as additional technical effects and advantages as readily understood by the skilled person in view of the following detailed description.

In one embodiment, the device is configured to cause a reversal of a pumping direction of the blood pump between the first and second operating states, so as to change the flow direction of the blood through the blood compartment of the dialyzer between the first and second operating states.

In one embodiment, the device is configured to cause at least one flow switching device in the treatment fluid flow circuit to change the flow direction of the treatment fluid through the treatment fluid compartment of the dialyzer between the first and second operating states. Optionally, during the measurement phase, the first and second access devices are connected to upstream and downstream portions, respectively, of the vascular access.

In one embodiment, the device is configured to, between the first and second operating states, cause at least one flow switching device in the treatment fluid flow circuit to change the flow direction of treatment fluid through the treatment fluid compartment of the dialyzer and cause the blood pump to reverse its pumping direction so as to change the flow direction of blood through the blood compartment of the dialyzer and the flow direction of blood through the first and second access devices.

In one embodiment, the device is configured to compute the measurement value of the comparison parameter to represent one of: a ratio of the treatment efficiencies in the first and second operating states, and a difference between the treatment efficiencies in the first and second operating states.

In one embodiment, the device is further configured to cause, by a first control signal, the treatment fluid flow circuit to generate an essentially fixed value of a fluid property of the treatment fluid that enters the dialyzer during the first and second operating states, the fluid property being measured by the at least one sensor. Further, the device may be configured to maintain, between the first and second operating states, the essentially fixed value of the fluid property. The device may be further configured to, based on the output signal, compute a first difference in the fluid property between an inlet and an outlet of the treatment fluid compartment in the first operating state, and a second difference in the fluid property between the inlet and the outlet of the treatment fluid compartment in the second operating state, and the device may be configured to compute the measurement value as a function of a quotient of the first and second differences. The device may be further configured to, in advance of the measurement phase, compute at least one of the first and second differences and, if the at least one of the first and second differences is lower than a predefined minimum value, control a source of treatment fluid in the treatment fluid flow circuit to adjust the fluid property of the treatment fluid so that the at least one of the first and second differences exceeds the predefined minimum value.

In one embodiment, the fluid property is a physical and/or chemical property of the treatment fluid.

In one embodiment, the fluid property is one of a temperature, an electrical conductivity, and a concentration of a substance that is present in the blood and is capable of exchanging across the semi-permeable membrane.

In one embodiment, the device is further configured to obtain dedicated settings for the blood pump and the treatment fluid flow circuit and apply the dedicated settings to cause, by a first control signal, the treatment fluid flow circuit to generate a fixed flow rate of treatment fluid through the dialyzer during the first and second operating states, and to cause, by a second control signal, the blood pump to generate an essentially fixed flow rate of blood through the dialyzer during the first and second operating states.

In one embodiment, the device is further configured to obtain, for first and second sets of control values of operating parameters of the blood treatment machine in the first and second operating states, a current function that relates the comparison parameter to the fluid flow rate in the vascular access, wherein the estimated value of the fluid flow rate in the vascular access is determined so that the current function yields the measurement value. In one implementation, the device is further configured to obtain, from an electronic memory, the current function among a set of predefined functions based on the first and second sets of control values. In an alternative implementation, the device is further configured to obtain a governing function from an electronic memory, and generate the current function by entering at least part of the first and second sets of control values into the governing function.

In one implementation, the current function is given by an algebraic function, or a numerical inverse thereof, wherein the algebraic function has the comparison parameter as output variable and the access flow rate as input variable and is derived for a hydraulic model of the blood treatment machine as connected to the patient and given a current flow direction of blood and treatment fluid through the dialyzer and a current flow direction of blood to the first and second access devices.

In one implementation, the first and second sets of control values comprise a flow rate of blood through the dialyzer in the first and second operating states, a flow rate of treatment fluid through the dialyzer in the first and second operating states, and one of a mass transfer area coefficient of the dialyzer and an in-vivo clearance of the blood treatment machine in one of the first and second operating states. In this implementation, the current function may be obtained for a generic value of cardiac output of the patient. Alternatively or additionally, the device may be configured to set the flow rate of blood through the dialyzer equal to or less than 100 ml/min, and preferably equal to or less than 50 ml/min, in the first and second operating states, wherein the control value for the mass transfer area coefficient is a generic value. The device may be further configured to cause the blood treatment machine to perform a second switch between the first and second operating states while applying third and fourth sets of control values which differ from the first and second sets of control values by at least the flow rate of blood through the dialyzer, acquire the output signal of the at least one sensor in the first and second operating states, and compute a second measurement value of the comparison parameter, and the device may be configured to determine two candidate values of the fluid flow rate for each of the measurement value and the second measurement value, and determine the estimated value of the fluid flow rate based on the candidate values, preferably the two most similar candidate values.

Alternatively, the device may be configured to set the flow rate of blood through the dialyzer to exceed 100 ml/min in the first and second operating states, wherein the control value for the mass transfer area coefficient is a specific value for the dialyzer. The current function may relate the comparison parameter to the fluid flow rate and cardiac output of the patient, and the device may be further configured to cause the blood treatment machine to perform a second switch between the first and second operating states while applying third and fourth sets of control values of the operating parameters, acquire the output signal of the at least one sensor in the first and second operating states, compute a second measurement value of the comparison parameter, obtain a second current function that relates the comparison parameter to the fluid flow rate and the cardiac output for the third and fourth sets of control values, and determine the estimated value of the fluid flow rate, and optionally an estimated value of the cardiac output, based on the current function set to yield the measurement value and the second current function set to yield the second measurement value.

In one implementation, the device is configured to determine the estimated value of the fluid flow rate, and optionally the estimated value of the cardiac output, by identifying an intersection between the current function and the second current function in a two-dimensional space defined by the fluid flow rate and the cardiac output.

In one embodiment, the at least one sensor is one of a concentration sensor, a temperature sensor, a conductivity sensor, an optical absorbance sensor, a polarimetry sensor and a density sensor.

A second aspect of the invention is a blood treatment machine, comprising an extracorporeal blood flow circuit with first and second access devices for connection to a vascular access of a patient and having a blood pump operable to generate a flow of blood from the first access device through a blood compartment of a dialyzer and to the second access device, and a treatment fluid flow circuit configured to generate a flow of treatment fluid through a treatment fluid compartment of the dialyzer, the treatment fluid compartment being separated from the blood compartment by a semi-permeable membrane. The blood treatment machine further comprises a device according to the first aspect.

A third aspect of the invention is a method of determining a fluid flow rate in a vascular access of a patient. The method comprises the step of connecting, to the vascular access, first and second access devices of an extracorporeal blood flow circuit in a blood treatment machine that comprises a blood pump operable to generate a flow of blood in the extracorporeal blood flow circuit from the first access device through a blood compartment of a dialyzer and to the second access device, the blood compartment being separated from a treatment fluid compartment of the dialyzer by a semi-permeable membrane and the blood treatment machine comprising a treatment fluid flow circuit configured to generate a flow of treatment fluid through the treatment fluid compartment. The method further comprises the steps of: causing the blood treatment machine to switch from a first operating state to a second operating state, wherein the second operating state at least differs from the first operating state by a change of flow direction of the blood or the treatment fluid through the dialyzer, acquiring an output signal of at least one sensor in the blood treatment machine in the first and second operating states, computing, based on the output signal, a measurement value of a comparison parameter that compares treatment efficiency in the first operating state to treatment efficiency in the second operating state, and determining, based on the measurement value, an estimated value of the fluid flow rate in the vascular access.

In one embodiment, the step of causing the blood treatment machine to switch from the first operating state to the second operating state comprises reversing a pumping direction of the blood pump, so as to change the flow direction of the blood through the blood compartment of the dialyzer between the first and second operating states.

In one embodiment, the step of causing the blood treatment machine to switch from the first operating state to the second operating state comprises operating at least one flow switching device in the treatment fluid flow circuit to change the flow direction of the treatment fluid through the treatment fluid compartment of the dialyzer between the first and second operating states. Optionally, the method comprises connecting the first and second access devices to upstream and downstream portions, respectively, of the vascular access.

In one embodiment, the step of causing the blood treatment machine to switch from the first operating state to the second operating state comprises operating at least one flow switching device in the treatment fluid flow circuit to change the flow direction of treatment fluid through the treatment fluid compartment of the dialyzer and reversing a pumping direction of the blood pump so as to change the flow direction of blood through the blood compartment of the dialyzer and the flow direction of blood through the first and second access devices.

In one embodiment, the measurement value of the comparison parameter is computed to represent one of: a ratio of the treatment efficiencies in the first and second operating states, and a difference between the treatment efficiencies in the first and second operating states.

In one embodiment, the method further comprises causing the treatment fluid flow circuit to generate an essentially fixed value of a fluid property of the treatment fluid that enters the dialyzer during the first and second operating states, and operating the at least one sensor to measure the fluid property in the first and second operating states. Further, the method may comprise maintaining the essentially fixed value of the fluid property between the first and second operating states. The method may further comprise computing, based on the output signal, a first difference in the fluid property between an inlet and an outlet of the treatment fluid compartment in the first operating state, and a second difference in the fluid property between the inlet and the outlet of the treatment fluid compartment in the second operating state, and computing the measurement value as a function of a quotient of the first and second differences. The method may further comprise initial steps of computing at least one of the first and second differences and, if said at least one of the first and second differences is lower than a predefined minimum value, adjusting the fluid property of the treatment fluid so that said at least one of the first and second differences exceeds the predefined minimum value.

In one embodiment, the method further comprises causing the treatment fluid flow circuit to generate a fixed flow rate of treatment fluid through the dialyzer during the first and second operating states, and causing the blood pump to generate an essentially fixed flow rate of blood through the dialyzer during the first and second operating states.

In one embodiment, the method further comprises obtaining, for first and second sets of control values of operating parameters of the blood treatment machine in the first and second operating states, a current function that relates the comparison parameter to the fluid flow rate in the vascular access, and determining the estimated value of the fluid flow rate in the vascular access so that the current function yields the measurement value. In one implementation, the method further comprises obtaining the current function among a set of predefined functions based on the first and second sets of control values. In another implementation, the method further comprises obtaining a governing function, and generating the current function by entering at least part of the first and second sets of control values into the governing function.

In one implementation, the current function is given by an algebraic function, or a numerical inverse thereof, wherein the algebraic function has the comparison parameter as output variable and the access flow rate as input variable and is derived for a hydraulic model of the blood treatment machine as connected to the patient and given a current flow direction of blood and treatment fluid through the dialyzer and a current flow direction of blood to the first and second access devices.

In one implementation, the first and second sets of control values comprise a flow rate of blood through the dialyzer in the first and second operating states, a flow rate of treatment fluid through the dialyzer in the first and second operating states, and one of a mass transfer area coefficient of the dialyzer and an in-vivo clearance of the blood treatment machine in one of the first and second operating states. In this implementation, the method may obtain the current function for a generic value of cardiac output of the patient. Alternatively or additionally, the method may set the flow rate of blood through the dialyzer equal to or less than 100 ml/min, and preferably equal to or less than 50 ml/min, in the first and second operating states, and obtain a generic value for the mass transfer area coefficient. The method may further comprise causing the blood treatment machine to perform a second switch between the first and second operating states while applying third and fourth sets of control values which differ from the first and second sets of control values by at least the flow rate of blood through the dialyzer, acquiring the output signal of the at least one sensor in the first and second operating states, and computing a second measurement value of the comparison parameter, wherein the method may further comprise determining two candidate values of the fluid flow rate for each of the measurement value and the second measurement value, and determining the estimated value of the fluid flow rate based on the candidate values, preferably the two most similar candidate values.

Alternatively, the method may set the flow rate of blood through the dialyzer to exceed 100 ml/min in the first and second operating states, and obtain a dialyzer-specific value of the mass transfer area coefficient. The current function may relate the comparison parameter to the fluid flow rate and cardiac output of the patient, and the method may further comprise causing the blood treatment machine to perform a second switch between the first and second operating states while applying third and fourth sets of control values of the operating parameters, acquire the output signal of the at least one sensor in the first and second operating states, computing a second measurement value of the comparison parameter, obtaining a second current function that relates the comparison parameter to the fluid flow rate and the cardiac output for the third and fourth sets of control values, and determining the estimated value of the fluid flow rate, and optionally an estimated value of the cardiac output, based on the current function set to yield the measurement value and the second current function set to yield the second measurement value.

In one implementation, the method comprises determining the estimated value of the fluid flow rate, and optionally the estimated value of the cardiac output, by identifying an intersection between the current function and the second current function in a two-dimensional space defined by the fluid flow rate and the cardiac output.

A fourth aspect of the invention is a computer-readable medium comprising computer instructions which, when executed by a processor, cause the processor to perform the method of the third aspect.

Any one of the above-identified embodiments of the first aspect may be adapted and implemented as an embodiment of the second to fourth aspects.

Still other objectives, features, aspects and advantages of the present invention will appear from the following detailed description, from the attached claims as well as from the drawings.

BRIEF DESCRIPTION OF THE DRAWINGS

Embodiments of the invention will now be described in more detail with reference to the accompanying schematic drawings.

DETAILED DESCRIPTION OF EXAMPLE EMBODIMENTS

Figure 1:
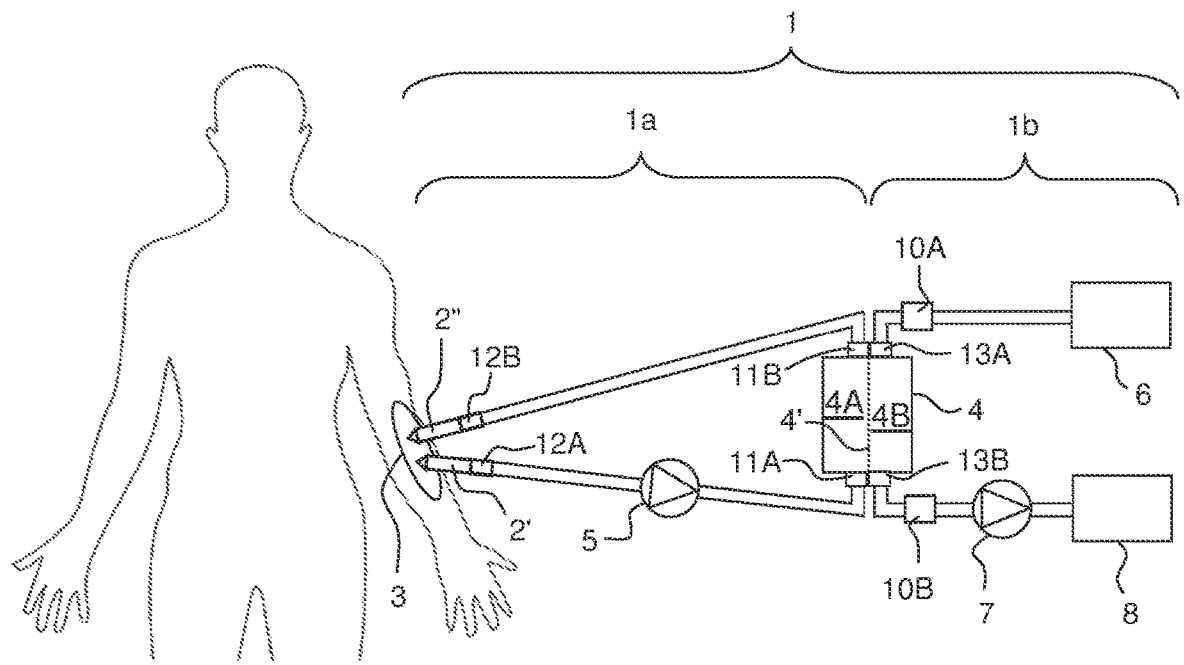
FIG. 1 is a schematic overview of a dialysis system connected to a patient.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Before describing embodiments of the invention detail, a few further definitions will be given.

As used herein, "clearance" is given its ordinary meaning and is a measure of the purification efficiency of a dialyzer, typically given as ml/min. Clearance may sometimes be defined to exclusively refer to removal, from the blood, of one or more substances that are absent in the fresh treatment fluid fed to the dialyzer, such as urea. The term "dialysance" may sometimes be used to designate an approximation of clearance so as to represent removal, from the blood, of one or more substances that are present also in the fresh treatment fluid, such as sodium or another electrolyte that passes the semi-permeable membrane of the dialyzer. With these definitions, the clearance and the dialysance will be equal for a given dialyzer in the absence of ultrafiltration. Within the present disclosure, no distinction is made between clearance and dialysance, and these terms are thus considered to be synonymous. Clearance may be measured directly on the dialyzer under well-controlled, non-patient specific, laboratory conditions. This type of clearance is commonly known as "in-vitro clearance" or "dialyzer clearance" and makes it possible to assess the relative efficacy of different dialyzers. Clearance may also be measured for a dialyzer under actual dialysis treatment conditions involving a patient. This type of clearance is a measure of treatment efficiency and is commonly known as "in-vivo clearance" or "effective clearance" and is influenced by, e.g., the dialyzer, the effective blood flow rate, ultrafiltration, recirculation, and the flow rate of treatment fluid. Unless explicitly stated otherwise, the term clearance refers to the in-vivo clearance in the following description.

FIG. 1 illustrates a human subject or patient which is connected to an extracorporeal blood flow circuit 1a by way of access devices 2', 2" inserted into a dedicated vascular access 3 (also known as "blood vessel access") on the subject. The extracorporeal blood flow circuit 1a (denoted "EC circuit" in the following) is configured to draw blood from the vascular access 3 via access device 2' and pump the blood through a blood filter unit 4 and back to the vascular access 3 via access device 2". Thus, access device 2' is designated for blood withdrawal and access device 2" is designated for blood return. The vascular access 3 may be a fistula or a graft provided in the forearm of the patient, and the access devices 2', 2" may be needles or catheters, as is well-known in the art. The blood filter unit 4 may be any type of filtering device, such as a coil dialyzer, a parallel plate dialyzer, a hollow fiber dialyzer, etc. For simplicity, the blood filter unit 4 is denoted "dialyzer" in the following. The dialyzer 4 defines a blood chamber 4A and a treatment fluid chamber 4B separated by a semipermeable membrane 4'.

The EC circuit 1a is part of an apparatus or machine 1 for blood treatment, such as a dialysis machine, at least when the machine 1 has been prepared for a treatment session. In the illustrated example, the EC circuit 1a comprises bloodlines connected to the access device 2', 2", a blood pump 5 and the blood chamber 4A of the dialyzer 4. As will be further described below, the blood pump 5 may be operable in both a forward (default) direction and a reverse direction. The skilled person realizes that FIG. 1 is a simplified illustration and that the EC circuit 1a may comprise further components, such as a venous drip chamber, one or more pressure sensors, clamps, valves, etc.

The machine 1 further comprises a supply system 1b for treatment fluid (denoted "TF circuit" in the following). The TF circuit 1b is arranged to pump a treatment fluid through the treatment fluid side 4B of the dialyzer 4, while the blood pump 5 is operated to pump blood through the blood side 4A of the dialyzer 4, whereby solutes are transported over the membrane 4' due to a concentration gradient and/or ultrafiltrate is transported over the membrane 4' due to a pressure gradient. In the illustrated example, the TF circuit 1b comprises a source 6 of fresh treatment fluid (e.g. dialysis fluid), various fluid lines, the treatment fluid chamber 4B of the dialyzer 4, a treatment fluid pump 7, and is connected to a receptacle/drain 8 for receiving spent treatment fluid. The skilled person understands that the TF circuit 1b may include a plurality of other functional components such as further pumps, balancing chambers, valves, mixing chambers, heaters, etc. In the particular example of FIG. 1, the TF circuit 1b also includes sensors 10A, 10B, which are configured to generate signals that allow a measurement unit (not shown) to estimate the flow rate of blood in the vascular access.

In practice, the machine 1 is typically formed as a combination of a permanent machine part and one or more disposables attached to the permanent machine part. The permanent machine part is enclosed in a machine chassis, often denoted "monitor", which exposes holders for mounting the disposable(s) in operative engagement with components such as connectors, pumps, sensors, clamps, etc. The disposables are exposed to the circulating blood in the EC circuit 1a and are typically discarded after each treatment session.

One such disposable is a bloodline set which includes the bloodlines of the EC circuit 1a, and connectors 11A, 11B on the bloodlines for coupling to dedicated inlet and outlet ports on the dialyzer 4, as indicated in FIG. 1. The access devices 2', 2" may also be integrated with the bloodlines in the bloodline set. Alternatively, the access devices 2', 2" may be provided as a separate disposable for connection to dedicated connectors 12A, 12B on the bloodlines, as indicated in the FIG. 1. The bloodline set may include further components, such as a venous drip chamber, valves, clamps, etc. For reasons of economy, components of the EC circuit 1a that are not exposed to the circulating blood are normally integrated in the machine chassis. For example, the blood pump 5 may be implemented as a peristaltic pump that engages with the exterior of a bloodline to push the blood though the bloodline, as is well known in the art. However, it is conceivable that the blood pump 5, if exposed to blood, is included in the disposable.

The dialyzer 4 may be provided as a separate disposable for installation on the machine chassis. When mounted on the machine chassis, the connectors 11A, 11B of the bloodline set are coupled to the dedicated inlet and outlet ports of the blood chamber 4A, and dedicated connectors 13A, 13B on the fluid lines of the TF circuit 1b are connected to dedicated inlet and outlet ports of the treatment fluid chamber 4B.

In an alternative, the dialyzer 4 is included in the bloodline set. In a further alternative, the bloodline set is replaced or supplemented by a cassette that defines internal fluid paths for blood. Such as cassette may also be integrated with the dialyzer.

Embodiments of the invention provide a technique for determining the flow rate of blood in the vascular access 3, commonly known as the "access flow rate" and designated by A herein. For example, the access flow rate A may be determined in connection with a treatment session, e.g. when the machine 1 has been prepared for a treatment session and connected to the vascular access 3, or at completion of a treatment session.

Figure 2A:
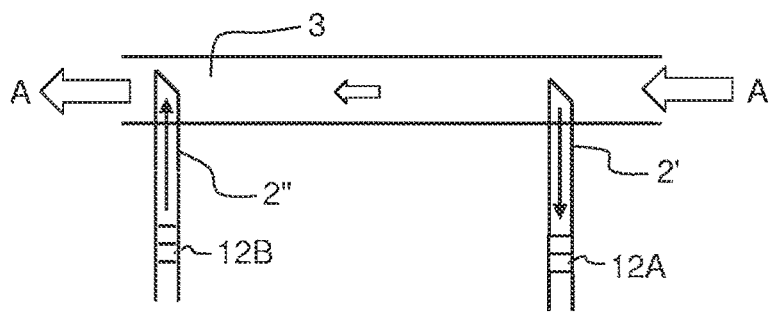
FIGS. 2A-2B are schematic side views of withdrawal and return devices in a normal and reversed configuration, respectively, at a vascular access.

As explained in the Background section, knowledge of the access flow rate may be essential to ensure proper blood treatment. To further explain the importance of the access flow rate, FIG. 2A schematically illustrates a vascular access 3 and access devices 2', 2" in a normal (correct) configuration. The blood flow in the vascular access 3 and access devices 2', 2" is indicated by arrows. In the normal configuration, the access device 2' for blood withdrawal is positioned at an upstream portion for extracting blood and the access device 2" for blood return is positioned at a downstream portion for returning blood to the vascular access 3. If the blood flow rate into the access device 2' exceeds the incoming blood flow rate to the vascular access 3, i.e. the access flow rate A, so-called recirculation may occur, which implies that the flow of blood in the vascular access 3 will be reversed and some of the already treated blood is again withdrawn by the access device 2' for blood treatment. By the recirculation, less blood flowing from the body into the vascular access 3 will be treated, leading to reduced treatment efficiency.

Figure 2B:
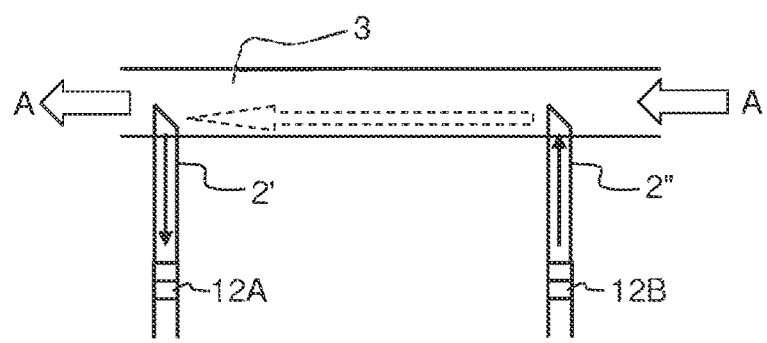

For the sake of completeness and to emphasize the importance of proper installation of the access devices 2', 2", FIG. 2B illustrates a reversed configuration of the access devices 2', 2". Here, the access device 2' is positioned at the downstream position and the access device 2" is positioned at the upstream position, with the consequence of treated blood being returned upstream and being extracted downstream. Thus, the reversed configuration inevitably results in recirculation, as indicated by a dashed arrow in FIG. 2B.

Figure 3A:
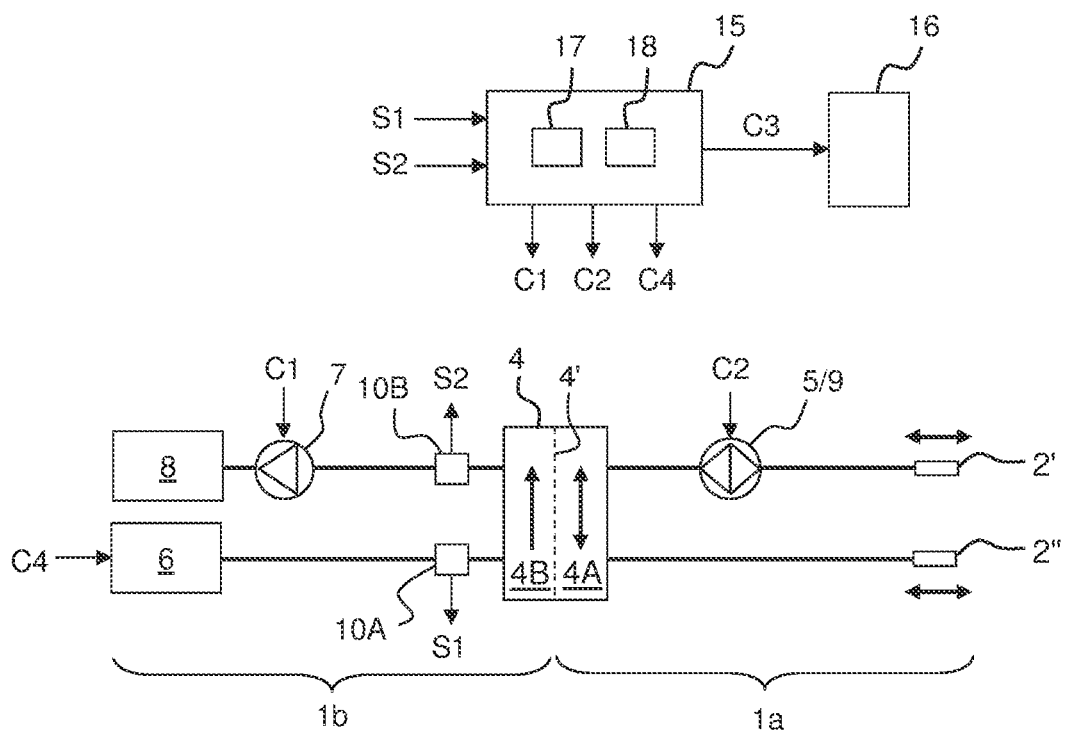
FIG. 3A is a block diagram of a dialysis system enabling flow direction switching in the dialyzer.

Embodiments of the invention are based on a finding that it is possible to calculate the access flow rate A based on a comparison of the in-vivo clearance of a dialysis machine before and after a flow reversal in the dialysis machine, and that the flow reversal need not be made in relation to the vascular access 3 but may be made in relation to the dialyzer 4, i.e. by reversing the flow direction of either blood or treatment fluid, or both, in the dialyzer 4. While, as shown below, a flow reversal in the dialyzer 4 may cause some computational complexity for calculating the access flow rate A, it entails other benefits that outweigh this drawback. For example, such a flow reversal may be made by use of standard components of a dialysis machine, e.g. by simply switching the pumping direction of the blood pump 5. Such an embodiment is shown in FIG. 3A and enables the use of a standard bloodline set or cassette in the EC circuit 1a. In an alternative, the flow reversal may be made by a flow switching device in the TF circuit 1b. Such an embodiment is shown in FIG. 3B and also enables the use of a standard bloodline set or cassette in the EC circuit 1a.

The embodiment in FIG. 3A includes an access flow rate measuring unit 15 (denoted control device or controller in the following) which is configured to control the operation of the machine 1 in FIG. 1, at least during a measurement phase for determining the access flow rate A in the vascular access 3 of a connected patient. The machine in FIG. 3A differs from the machine in FIG. 1 in that the blood pump 5 is reversible, i.e. operable in two pumping directions, as indicated by a double triangle icon. The controller 15 comprises a signal interface for input and output of signals. In the illustrated example, the controller 15 is configured to generate and output control signals C1, C2, C4 for the treatment fluid pump 7, the blood pump 5, and the source 6 of treatment fluid, and to receive and process measurement signals S1, S2 from sensors 10A, 10B arranged in the TF circuit 1b, on both sides of the treatment fluid chamber 4B. The controller 15 may also be connected, by wire or wirelessly, to a user interface (UI) device 16 for interacting with the operator of the machine 1. The controller 15 is configured to generate and output a control signal C3 for operating the UI device 16, e.g. to generate warning or alarm signals (audible and/or visible), display messages with information or instructions for the operator, display calculated access flow rate, etc. The UI device 16 may also be operable by the controller 15 to receive input from the operator. The UI device 16 may thus comprise one or more of a display, a touch panel, a loudspeaker, a microphone, a keyboard, a mouse, an indicator lamp, etc. It is understood that the UI device 16 may be (part of) a conventional user interface on the machine 1.

The operation of the controller 15 may be at least partly controlled by software instructions that are supplied on a computer-readable medium for execution by a processor 17 in conjunction with an electronic memory 18 in the controller 15. In particular, the controller 15 is configured to, by control signal C2, control the blood pump 5 to either operate in a default, forward direction or a reverse direction. The control signal C2 may also set the speed of the blood pump 5 and thus the flow rate of blood in the EC circuit 1a. By control signal C1, the controller 15 sets the speed of the treatment fluid pump 7 and thus the flow rate of treatment fluid through the dialyzer 4. By control signal C4, the controller 15 may set a property of the treatment fluid provided by the source 6, e.g. the temperature and/or the composition. As indicated by double-ended arrows in the dialyzer 4 and adjacent to the access devices 2', 2", a switching of the blood pump 5 between the forward and reverse directions causes a simultaneous change of the flow direction in the blood compartment 4A and through the access devices 2', 2".

Figure 3B:
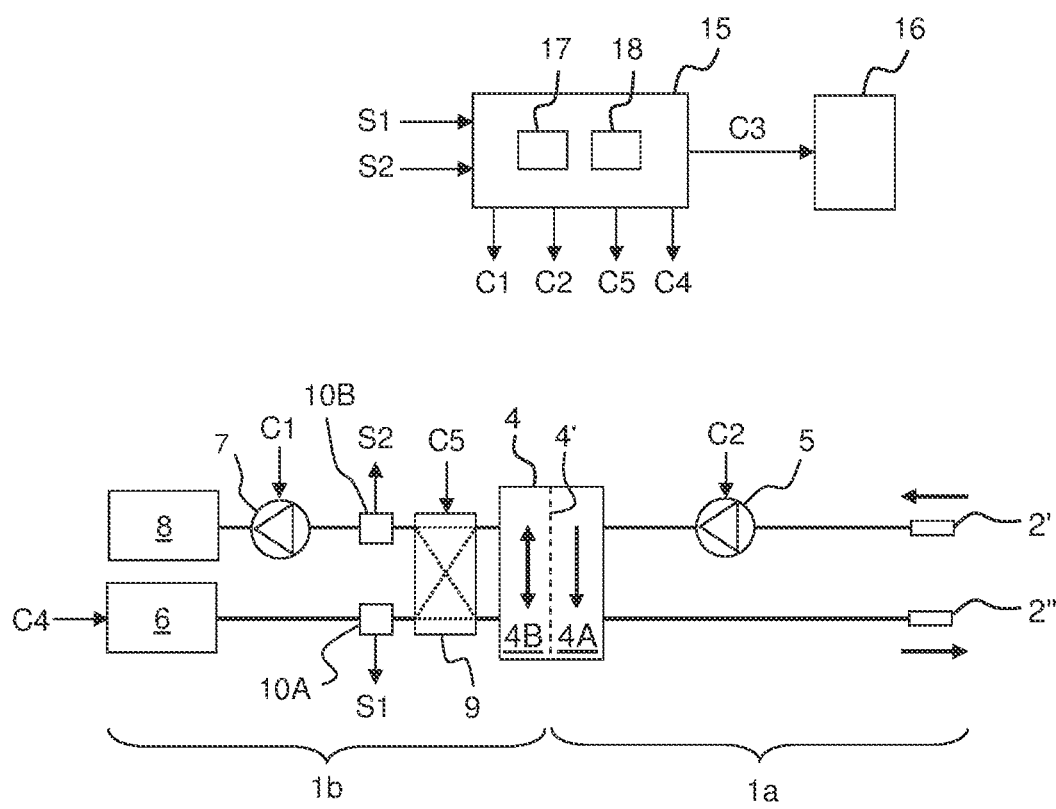
FIG. 3B is a block diagram of a variant.

The machine in FIG. 3B differs from the machine in FIG. 1 in that a flow switching device (FSD) 9 is installed in the TF circuit 1b, intermediate the sensors 10A, 10B and the inlet and outlet ports of the treatment fluid chamber 4B. The FSD 9 is operable in two configurations with different flow paths of treatment fluid to and from the dialyzer 4: a first configuration with straight paths through the FSD 9 so as to provide a flow of treatment fluid from bottom to top in the chamber 4B in FIG. 3B, and a second configuration with crossed paths so as to provide a flow of treatment fluid from top to bottom in the chamber 4B in FIG. 3B. This type of FSD 9 is well-known in the art. For example, the FSD 9 may be implemented as a combination of fluid lines and a plurality of valves, or by a single dedicated valve of the type shown in U.S. Pat. No. 7,896,831. It should be noted that the FSD 9 is only in contact with treatment fluid and may be installed as a permanent component within the chassis of the machine 1.

The machine in FIG. 3B is operated, during the measurement phase, by the controller 15 in the same way as described for the machine in FIG. 3A, with the difference that the controller 15 is operable to generate a control signal C5 for the FSD 9 to change the flow direction in the treatment fluid chamber 4B. The blood pump 5 may or may not be reversible.

Figure 4:
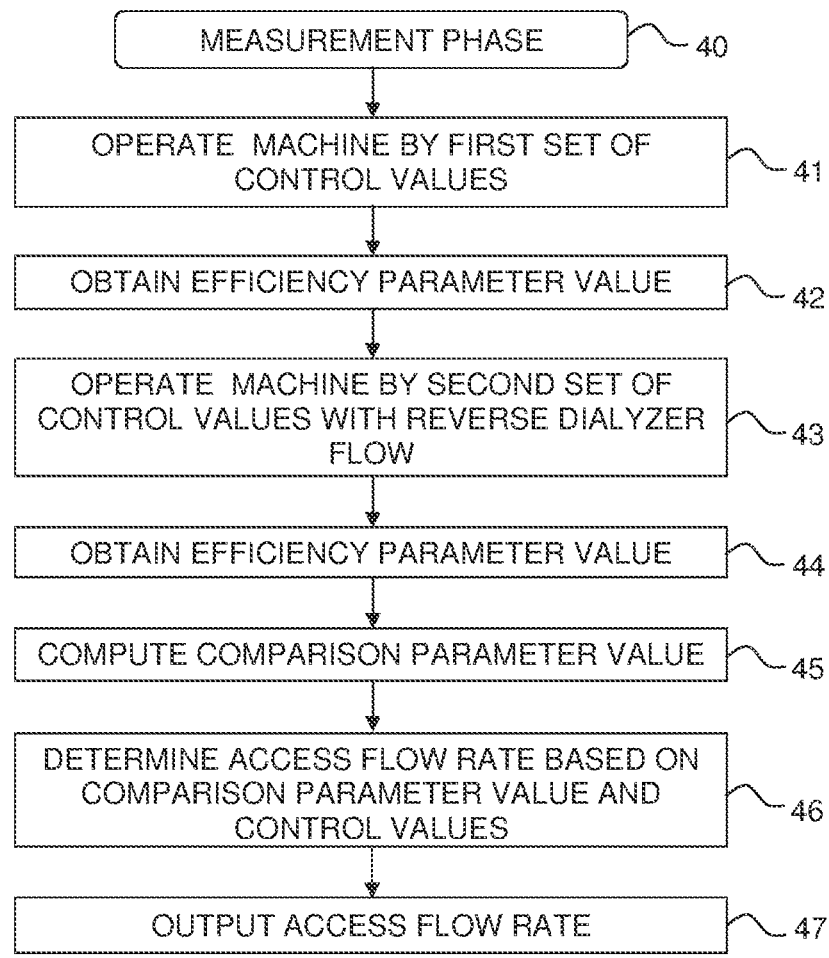
FIG. 4 is a flow chart of a method implemented by a controller in FIGS. 3A-3B.

Various principles, embodiments, implementations and examples of the present invention will be described with reference to FIG. 4, which shows an embodiment of a measurement phase 40 performed by the controller 15. FIG. 4 will be described with further reference to the embodiments in FIGS. 3A-3B.

In step 41, the machine 1 is set to operate in a first operating state, which is given by a first set of control values, i.e. current values of relevant operating parameters. Such operating parameters may include the flow rate of blood (designated by B herein), the flow rate of treatment fluid (designated by D herein), a property of the treatment fluid (e.g. composition or temperature), and a flow direction (e.g. a pumping direction of the blood pump 5 or a setting of the FSD 9). In the embodiments of FIGS. 3A-3B, the operating parameters are set by control signals C1, C2, C4, C5.

In step 42, the controller 15 computes, at least partly based on the output signals S1, S2 from the sensors 10A, 10B, a current value of an efficiency parameter that represents the in-vivo clearance of the machine 1 in the first operating state. In one implementation, the efficiency parameter is explicitly given as the in-vivo clearance (designated by $K_{eff}$ herein), or as a function thereof. The current value of $K_{eff}$ may be obtained by the bolus technique discussed in the Background section. In another implementation, which obviates the need to perform a dedicated measurement procedure for determining $K_{eff}$, the current value of the efficiency parameter is set to, or as a function of, the difference between the property measured by the sensors 10A, 10B, i.e. the difference between the measurement signals S1, S2. This difference is designated by $\Delta C$ in the following. It is important to note that the difference $\Delta C$ is determined without any bolus change in the measured property. The use of the difference $\Delta C$ will be explained and motivated further below with reference to FIGS. 6A-6C.

In step 43, the machine 1 is set to operate in a second operating state, which is given by a second set of control values. The second set of control values relates to the same operating parameters as the first set of control values. The second operating state differs from the first operating state by at least the flow direction in the dialyzer 4. Thus, in FIG. 3A, the blood pump 5 is operated in different pumping directions in the first and second operating states. In FIG. 3B, the FSD 9 is set in different configurations in the first and second operating states.

In step 44, the controller 15 computes, at least partly based on the output signals S1, S2 from the sensors 10A, 10B, a current value of the efficiency parameter for the machine 1 in the second operating state.

In step 45, the controller 15 computes a value of a comparison parameter based on the current values obtained in steps 42 and 44. The comparison parameter may be a ratio of the current values, or a function of such a ratio. In the following, such a comparison parameter is denoted "efficiency ratio", and the value of the efficiency ratio is denoted "measured ratio" or "measurement value" and is designated by $m_1$.

In step 46, the controller 15 determines a current value $A_m$ of the access flow rate based on the measured ratio $m_1$ and based on the first and second sets of control values. As will be shown in relation to FIGS. 6A-6C, it is not possible to obtain an algebraic expression for access flow rate as a function of efficiency ratio, at least not by solving the governing equations analytically. In general terms, the in-vivo clearance in the first and second operating states is governed by a respective governing function $f_1(A, CO, k_0A, D, B)$ and $f_2(A, CO, k_0A, D, B)$, with A being the access flow rate, CO being the cardiac output of the patient, $k_0A$ being a characteristic parameter of the dialyzer (mass transfer area coefficient), D being the flow rate of treatment fluid through the dialyzer, and B being the flow rate of blood through the dialyzer. It should be understood that the governing functions $f_1$, $f_2$ are determined with knowledge of the flow direction of blood in relation to the vascular access 3 and the flow directions of blood and treatment fluid in the dialyzer 4 in the respective operating state. The efficiency ratio R is governed by $f_1(A, CO, k_0A, D, B)/f_2(A, CO, k_0A, D, B)$, or the inverse thereof. This may be written as $R=f_3(A, CO, k_0A, D, B)$, with $f_3$ being a governing function given by $f_1$ and $f_2$. Under certain conditions (below), the governing function $f_3$ is equally valid when the efficiency parameter is given by the difference C.

At step 46, the flow directions in the first and second operating states as well as the values of D and B in the first and second operating states are known to the controller 15. Thus, in step 46, the controller 15 may enter the values of D and B into the appropriate governing function $f_3$ to obtain a current ratio function $f_c$ ("current function") for the measurement phase 40: $R=f_c(A, CO, k_0A)$. As will be discussed in more detail in relation to FIGS. 8-12, the controller 15 may also enter generic (standard) or actual values of the cardiac output CO and the characteristic parameter $k_0A$ into the governing function $f_3$ to yield $R=f_c(A)$. Alternatively, one or more ratio functions $f_c$ may be pre-computed and stored in an electronic memory that is accessible to the controller 15, e.g. memory 18, thereby allowing the controller 15 to retrieve the current function $f_c$ from memory in step 46. Each such pre-computed ratio function $f_c$ may be stored in association with associated control values, allowing the controller 15 to retrieve the current function $f_c$ that corresponds to the machine settings (control values) in step 41 and 43.

Figure 5:
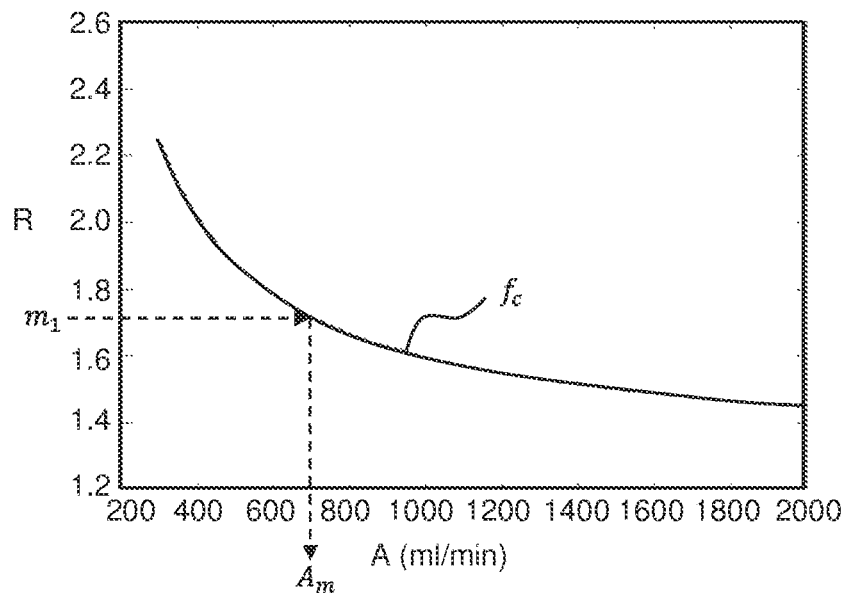
FIG. 5 illustrates determination of access flow rate based on a measured efficiency ratio and using a current function that relates efficiency ratio to access flow rate for a given measurement setting of a dialysis system.

It should be noted that the current function $f_c$ has the efficiency ratio R as dependent variable (output) and the access flow rate A as independent variable (input), whereas step 45 generates the measured ratio $m_1$. To obtain the current value $A_m$ that corresponds to the measured ratio $m_1$, step 46 may e.g. operate an iterative approach on the current function $f_c$ to find a value of A that renders $f_c=m_1$, as is well-known to the person skilled in numerical methods. FIG. 5 illustrates the general principle of determining the current value $A_m$ for the measured ratio $m_1$ and using the current function $f_c$. As an alternative to performing real-time operations on the current function $f_c$, one or more inverse ratio functions $f_c^{-1}$ may be pre-computed (e.g. by numerical methods) for each possible ratio function $f$ and stored in electronic memory, in analogy with the pre-computed ratio functions $f_c$ discussed above. Thereby, step 46 may be implemented to retrieve a current function $f_c^{-1}$ and obtain the current value of the access flow rate as: $A_m=f_c^{-1}(m_1)$.

In step 47, the controller 15 may output the current value $A_m$ of the access flow rate, e.g. to the UI device 16 for display or to a data logger. Alternatively or additionally, the controller 15 may store the current value $A_m$ in internal memory 18.

It is understood that the determination in step 46 presumes that the machine 1 generates certain fluid flow directions in the dialyzer 4 and a certain blood flow direction in relation to the vascular access 3 during the first and second operating states. Generally, the flow directions define a "flow direction status" at the dialyzer 4 and the vascular access 3, respectively. The flow direction status at the dialyzer 4 may be either "counter-current", in which blood and treatment fluid flow in opposite directions along the membrane 4', or a "co-current", in which blood and treatment fluid flow in the same direction along the membrane 4'. The flow direction status at the vascular access 3 may be either "normal", in which blood is taken from an upstream position and returned at a downstream position (FIG. 2A), or a "reversed", in which blood is taken from the downstream position and returned at the upstream position (FIG. 2B). During treatment, for maximum treatment efficiency, the flow direction status should be counter-current at the dialyzer 4 and normal at the vascular access 3. However, it is conceivable that the dialyzer 4 is connected, e.g. by oversight or deliberately, such that the flow direction status is co-current at the dialyzer 4 and/or reversed at the vascular access 3. To increase the reliability of the determined access flow rate, step 41 may involve a procedure to verify or determine the flow direction status at the dialyzer 4 and the vascular access 3. For example, the operator may be instructed via the UI device 16 to physically inspect the connections at the dialyzer 4 and the vascular access 3 and confirm desired connection states, or to manipulate the connectors 11A, 11B, 12A, 12B, 13A, 13B or the access devices 2', 2" to attain a desired flow direction status at the dialyzer 4 and the vascular access 3, respectively. Alternatively, the procedure may automatically detect the flow direction status at the dialyzer 4 and the vascular access 3, and optionally instruct the operator to make any required changes. In yet another alternative, the controller 15 is configured to obtain an appropriate current function $f_c$, $f_c^{-1}$ based on information about the respective flow direction status, either provided by the user or by the automatic detection.

Figure 6A:
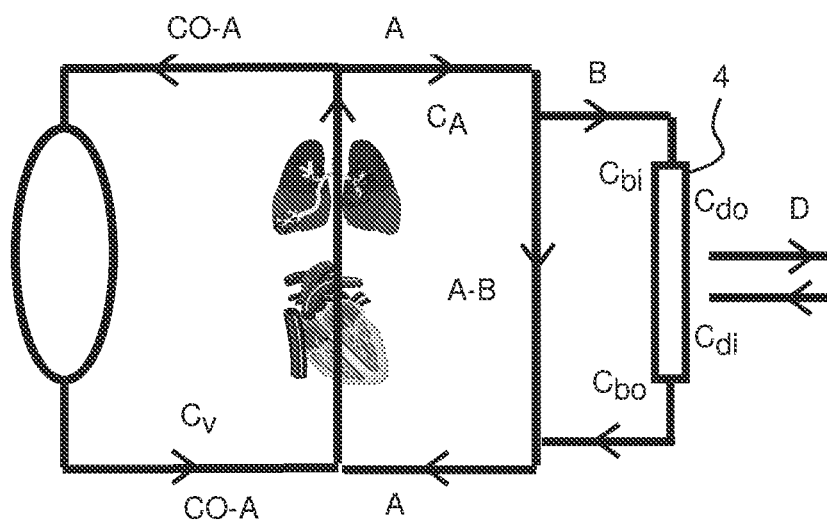
FIG. 6A is a hydraulic model of a patient connected to a dialysis system by access devices in a normal configuration, with counter-current flow in the dialyzer and without recirculation in the vascular access, FIG. 6B corresponds to FIG. 6A for a situation with recirculation in the vascular access, and FIG. 6C corresponds to FIG. 6A for a situation with the access devices in a reversed configuration.
Figure 6B:
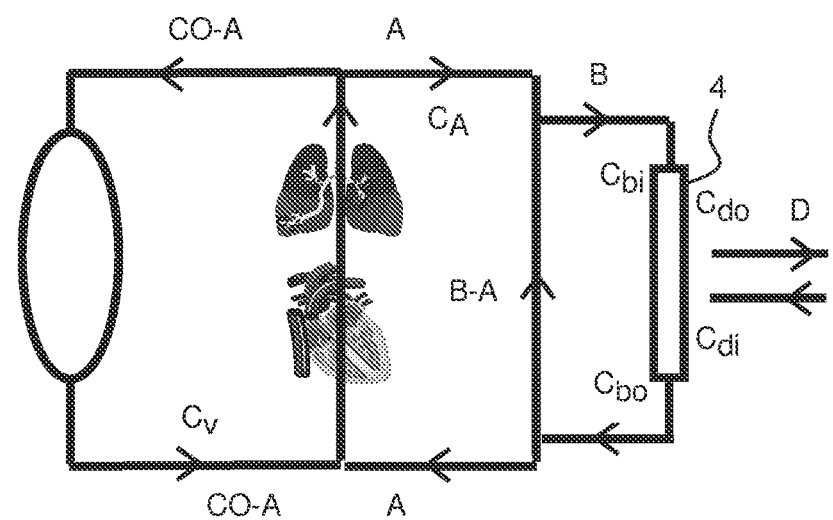
Figure 6C:
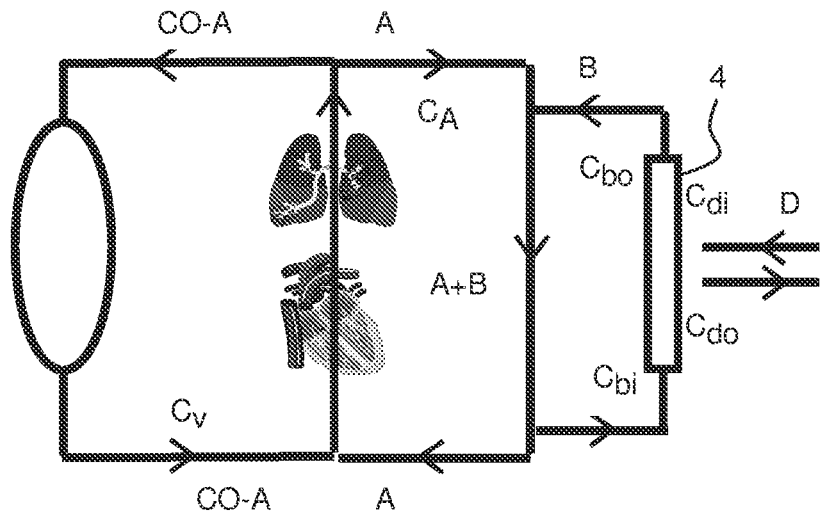

FIGS. 6A-6C illustrate a hydraulic model of a patient connected to a dialysis system for three different flow conditions in the vascular access. Below follows a formal analysis of the hydraulic model to derive expressions for the efficiency parameter for co-current and counter-current flow in the dialyzer 4, and for the access devices 2', 2" in normal and reversed position. The formal analysis considers both large and small access flow rates, to account for recirculation within the vascular access 3 also when the access devices 2', 2" are in the normal (correct) position. The formal analysis results in expressions for the above-mentioned governing functions $f_1$, $f_2$, and thereby also the governing function $f_3$. While the analysis assumes that the ultrafiltration rate is zero, the conclusions are sufficiently correct also in the presence of ultrafiltration. All flow rates below refer to blood water, which typically represents 85-90% of the total blood volume. This means that the determined access flow rate also refers to blood water and may be increased by 10-15% to relate to whole blood.

The following notation is used:
CO Cardiac Output (water flow rate)
A Access blood water flow rate
B Blood water flow rate to dialyzer
D Treatment fluid flow rate to dialyzer
$k_0A$ Mass transfer area coefficient of dialyzer (water value)
K Dialyzer clearance
$C_{bi}$ Blood water conductivity at dialyzer inlet
$C_{bo}$ Blood water conductivity at dialyzer outlet
α Donnan factor
$C_A$ Blood water conductivity in blood access
$C_v$ Blood water conductivity in venous blood from body
$C_{di}$ Treatment fluid conductivity at dialyzer inlet
$C_{do}$ Treatment fluid conductivity at dialyzer outlet For simplicity, the ultrafiltration rate is assumed to be zero. In this case, the dialyzer clearance K in the counter-current configuration is:

$$K = \frac{B \cdot D \cdot (1-g)}{D - f \cdot B} \quad (1)$$

with $$g = \exp(k_0 A \cdot (1/D - 1/B)) \quad (2)$$

In the co-current configuration, the dialyzer clearance K is $$K = \frac{B \cdot D \cdot (1-g)}{B + D} \quad (3)$$

with $$g = \exp(-k_0 A \cdot (1/D + 1/B)) \quad (4)$$

The transport from blood to treatment fluid can be expressed in three ways, looking at what leaves the blood side, enters the dialysis fluid side or crosses the membrane, respectively:

$$B \cdot (C_{bi} - C_{bo}) = D \cdot (C_{do} - C_{di}) = K \cdot (\alpha \cdot C_{bi} - C_{di}) \quad (5)$$

These expressions are independent of the flow direction status at the dialyzer as long as the correct value for dialyzer clearance K is used (counter-current or co-current). Eq. (5) provides an expression for the conductivity difference ΔC in the treatment fluid:

$$\Delta C = C_{do} - C_{di} = \frac{K}{D} \cdot (\alpha \cdot C_{bi} - C_{di}) \quad (6)$$

It is important to note that K designates the dialyzer clearance, not the in-vivo clearance. The following formal analysis will show that the conductivity difference ΔC is not only directly proportional to the dialyzer clearance K, as indicated by Eq. (6), but also to the in-vivo clearance. The formal analysis aims at expressing Eq. (6) as a function of $C_v$, which may be considered invariant of flow direction status at the dialyzer and the vascular access, instead of $C_{bi}$, which is affected by recirculation in the vascular access.

A first part of the formal analysis is based on FIG. 6A, which illustrates fluid flows in the hydraulic model with the access devices in the normal position and with an access flow rate that exceeds the blood water flow rate in the EC circuit (i.e. A>B). In this case, $C_{bi}$ is equal to $C_A$. A relation between $C_A$ and $C_v$ is given by a mass balance analysis at the joint before the heart-lung system, where the blood from the body with concentration $C_v$ is mixed with cleaned blood returning from the vascular access:

$$CO \cdot C_A = (CO - A) \cdot C_v + A \cdot C_A - D \cdot \Delta C \qquad (7)$$

where the mass in the cleaned blood from the vascular access is calculated by subtracting the mass removed in the dialyzer (expressed as D·ΔC) from the mass going to the access from the heart. Eq. (7) is valid for all configurations and yields:

$$C_A = C_v - \frac{D}{CO - A} \cdot \Delta C \qquad (8)$$

Inserting Eq. (8) into Eq. (6), with $C_A = C_{bi}$, and solving for ΔC yields:

$$\Delta C = \frac{1}{1 + \frac{\alpha \cdot K}{CO - A}} \cdot \frac{K}{D} \cdot (\alpha \cdot C_v - C_{di}) \qquad (9)$$

with K being given by Eq. (1) or (3) above, depending on flow direction status at the dialyzer (counter-current or co-current).

A second part of the formal analysis is based on FIG. 6B, which illustrates fluid flows in the hydraulic model with the access devices in the normal position but with an access flow rate that is lower than the blood water flow rate in the EC circuit (i.e. A<B). This means that part of the treated blood that is returned to the vascular access will be recirculated back into EC circuit. In this case, a mass balance analysis yields:

$$B \cdot C_{bi} = A \cdot C_A + (B - A) \cdot C_{bo} \qquad (10)$$

$$B \cdot C_{bo} = B \cdot C_{bi} - D \cdot \Delta C \qquad (11)$$

Combining Eq. (10), (11), (6) and (8) yields:

$$\Delta C = \frac{\beta}{1 + \beta \cdot \frac{\alpha \cdot K}{CO - A}} \cdot \frac{K}{D} \cdot (\alpha \cdot C_v - C_{di}) \qquad (12)$$

with $$\beta = \frac{A \cdot B}{A \cdot B + \alpha \cdot K \cdot (B - A)} \qquad (13)$$

Eq. (9) and (12) may be summarized in one equation covering all values of A:

$$\Delta C = \min\left(\frac{1}{1 + 1 \cdot \frac{\alpha \cdot K}{CO - A}}, \frac{\beta}{1 + \beta \cdot \frac{\alpha \cdot K}{CO - A}}\right) \cdot \frac{K}{D} \cdot (\alpha \cdot C_v - C_{di}) \qquad (14)$$

A third part of the formal analysis is based on FIG. 6C, which illustrates fluid flows in the hydraulic model with the access devices in reversed position. In this case, a mass balance analysis yields:

$$A \cdot C_{bi} = A \cdot C_A - D \cdot \Delta C \qquad (15)$$

Combining Eq. (15), (6) and (8) yields:

$$\Delta C = \frac{A \cdot (CO - A)}{A \cdot (CO - A) + \alpha \cdot K \cdot CO} \cdot \frac{K}{D} \cdot (\alpha \cdot C_v - C_{di}) \qquad (16)$$

Both Eq. (14) and (16) may be rewritten as:

$$\Delta C = \frac{K_{eff}}{D} \cdot (\alpha \cdot C_v - C_{di}) \qquad (17)$$

where $K_{eff}$ is the in-vivo clearance ("effective clearance"). Eq. (17) shows that the conductivity difference ΔC is representative of the in-vivo clearance $K_{eff}$, and thus treatment efficiency. It should be noted that both the Donnan factor α (which is close to 1) and the blood concentration $C_v$ are effectively unaffected by changes in flow direction status at the dialyzer and the vascular access. Thus, provided that the inlet conductivity $C_{di}$ is the same in the first and second operating states at steps 41 and 43 in FIG. 4, the factor $(\alpha \cdot C_v - C_{di})$ in Eq. (14) and (16) is invariant between the first and second operating states. If the conductivity difference ΔC is used as efficiency parameter at steps 42 and 44 in FIG. 4, the governing function $f_3$ for the efficiency ratio R is obtained by dividing two functions that are given by Eq. (14) and/or (16), with K according to either Eq. (1) or (3), depending on flow direction status in the first and second operating states, respectively. Thereby, the governing function $f_3$ will be independent of the factor $(\alpha \cdot C_v - C_{di})$. Generally, this formal analysis shows that the efficiency ratio R, when given by a ratio of conductivity differences ΔC, is governed by $R = f_3(A, CO, k_0 A, D, B)$.

In one non-limiting example, the machine 1 in FIG. 3A is switched from a first operating state with counter-current flow in the dialyzer 4 and with the access devices 2', 2" in the normal position, to a second operating state with co-current flow in the dialyzer 4 and with the access devices 2', 2" in the reversed position. In this example, the governing function $f_3$ is obtained by dividing Eq. (14) with Eq. (16), where K is given by Eq. (1) in Eq. (14) and by Eq. (3) in Eq. (16). The current function $f_c$ is obtained by entering at least the control values of D and B in the first and second operating states into Eq. (14) and Eq. (16), respectively. It should be noted that the control values of D and B may differ between the first and second operating states. However, it is generally desirable to maintain the same flow rates of blood and treatment fluid in the first and second operating states, to minimize the risk for unwanted fluctuations in the operational parameters that may negatively affect the accuracy of the determined access flow rate.

Reverting to Eq. (14), (16) and (17), it should be realized that the efficiency ratio R may alternatively be given by measured values of the in-vivo clearance $K_{eff}$ in the first and second operating states (steps 42, 44 in FIG. 4), where the in-vivo clearance $K_{eff}$ may be measured by any conventional technique. The governing function $f_3$ may still be given in the format $R=f_3(A, CO, k_0A, D, B)$. In a variant, the in-vivo clearance $K_{eff}$ is measured in only one of the first and second operating states, and the conductivity difference $\Delta C$ is measured in the other of the first and second operating states. As is well known to the skilled person, a conventional measurement of in-vivo clearance $K_{eff}$ also yields a value of $\alpha \cdot C_v$, which may be considered invariant between the first and second operating states. Thereby, the measured conductivity difference $\Delta C$ may be converted into in-vivo clearance $K_{eff}$ by use of Eq. (17). Thus, the efficiency ratio R may be formed based on $K_{eff}$ as measured in one operating state, and $K_{eff}$ calculated from $\Delta C$ as measured in the other operating state.

In summary, the foregoing analysis indicates that the conductivity difference $\Delta C$ is applicable for use as an efficiency parameter in the measurement phase 40, provided that the conductivity $C_{di}$ of treatment fluid at the inlet to the dialyzer 4 is controlled to be essentially unchanged during and between steps 42 and 44. In this context, "essentially unchanged" means that slight variations in $C_{di}$ are allowed to the extent that the resulting change in $\Delta C$ is small compared to the change caused by the switch between the first and second operating states. Typically, a $\Delta C$ change of ±1%, ±2% or ±5% caused by variations in $C_{di}$ is deemed small.

Reverting now to the measurement phase 40 in FIG. 4, step 42 may involve acquiring a respective first sensor value from the sensors 10A, 10B and computing a first $\Delta C$ value from the difference between the first sensor values, step 44 may involve acquiring a respective second sensor value from the sensors 10A, 10B and computing a second $\Delta C$ value from the difference between the second sensor values, and step 45 may involve computing the efficiency ratio by dividing the first $\Delta C$ value by the second $\Delta C$ value. The first and second sets of control values used in steps 41 and 43 may be predefined and retrieved by the controller 15 from memory 18.

It should be noted that a change of flow direction in the dialyzer 4 will not cause a change in measured conductivity difference $\Delta C$ if the inlet conductivity is equal to the plasma conductivity of the patient, i.e. $C_{di}=\alpha \cdot C_v$ in Eq. (17). Thus, it may be preferable, before initiating the measurement phase 40, to verify that the measured conductivity difference $\Delta C$ exceeds a minimum value, which may be predefined to yield a sufficient accuracy of the access flow rate. For example, the controller 15 may operate the machine 1 in the first or second operating state, using predefined values of B, D and $C_{di}$, compute a $\Delta C$ value based on the measurement signals S1, S2 and compare the $\Delta C$ value to the minimum value. If the $\Delta C$ value is less than the minimum value, the controller 15 operates the source 6, by generating the control signal C4, to adjust the inlet conductivity $C_{di}$ so that the $\Delta C$ value exceeds the minimum value. It is conceivable that this adjustment is made for $\Delta C$ values computed for both the first operating state and the second operating state. The verification is a preparatory procedure, which is completed in advance of the measurement phase 40 in FIG. 4. The measurement phase 40 is then conducted with the predefined values of B, D and with the inlet conductivity $C_{di}$ given by the verification.

It should also be understood that the upstream sensor 10A may be omitted if the inlet conductivity $C_{di}$ is otherwise known to the control unit 15, e.g. from the settings of the TF circuit 1b (e.g. via control signal C4).

The foregoing discussion has presumed that $\Delta C$ is a difference in electrical conductivity given by conductivity sensors 10A, 10B, which are responsive to ions in the treatment fluid. In practice, conductivity sensors will effectively indicate the concentration of ionized sodium in the treatment fluid. However, $\Delta C$ may represent a difference in another property of the treatment fluid. For example, the sensors 10A, 10B may be dedicated concentration sensors that are configured to measure the concentration of a specific marker substance in the treatment fluid. The marker substance may be any substance that is present in the blood and is capable of exchanging across the semi-permeable membrane 4', such as urea, creatinine, vitamin B12, beta-two-microglobuline, NaCl, or any ion or combination of ions. In another alternative, the sensors 10A, 10B may be absorbance sensors configured to determine optical absorbance as a measure of concentration. In still another alternative, the sensors 10A, 10B may be polarimetry sensors configured to determine polarization as a measure of concentration of an optically active substance, such as glucose, that rotates the plane of linearly polarized light. In still another alternative, the sensors 10A, 10B may be density sensors configured to measure the density (mass per unit volume) of the treatment fluid. According to yet another alternative, the sensors 10A, 10B may be temperature sensors configured to measure the temperature of the treatment fluid.

As explained in connection with step 46 in FIG. 4, the current function is generally given as $R=f_c(A, CO, k_0A)$. Below follows, with reference to FIGS. 7-12, examples of how this function may be parameterized and/or used to obtain the current value $A_m$ of the access flow rate based on a measured ratio $m_1$, and how the first and second set of control values may be chosen for steps 41 and 43 to improve the accuracy of the current value $A_m$. Examples are given both for a first embodiment with blood pump reversal, e.g. the machine 1 in FIG. 3A, and a second embodiment with reversal of treatment fluid flow, e.g. the machine 1 in FIG. 3B. It should be noted that all graphs in FIGS. 7-12 show inverse ratio functions $f_c^{-1}$ which represent a ratio of conductivity differences $\Delta C$ and are computed based on Eq. (14) and (16) above. The examples also presume that the control values $C_{di}$, B, D are the same in steps 41 and 43, i.e. that the first and second operating states only differ by flow direction status.

Blood Pump Reversal

In the first embodiment with blood pump reversal, it is preferable that either the first or the second operating state involves a flow direction status that is counter-current at the dialyzer 4 and normal at the vascular access 3, i.e. the same flow direction status that is used during regular treatment. Thereby, there is no need to change the connections at either the dialyzer 4 or at the access devices 2', 2" between the measurement phase 40 and regular treatment. Nevertheless, it is conceivable that either the first or the second operating state involves a flow direction status that is co-current at the dialyzer 4 and reversed at the vascular access.

In the following examples, however, it is assumed that the dialyzer 4 and the vascular access 3 are correctly connected in the first operating state, i.e. that the flow direction status is counter-current at the dialyzer 4 and normal at the vascular access 3. In the second operating state, after the blood pump reversal, the flow direction status is co-current at the dialyzer 4 and reversed at the vascular access 3.

Figure 7A:
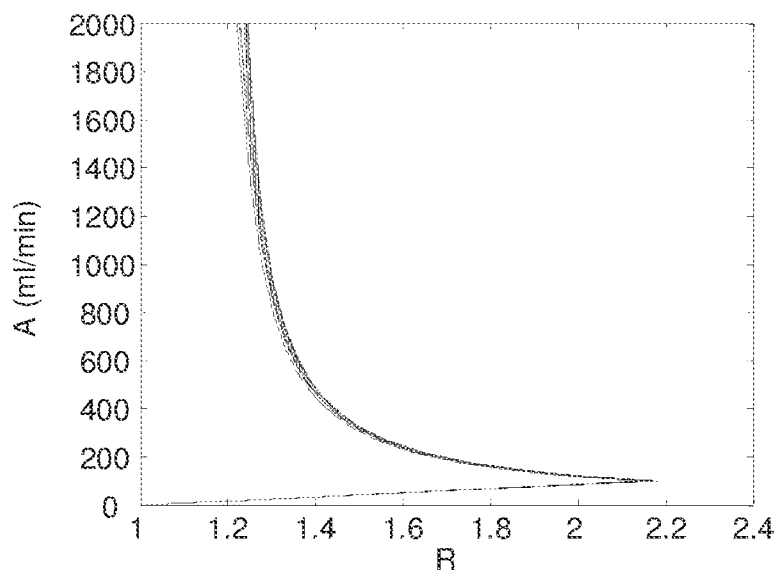
FIG. 7A is a plot of a current function obtained at a blood flow rate of 100 ml/min for various types of dialyzers and cardiac output values and a given measurement setting of the dialysis system in FIG. 3A, FIG. 7B corresponds to FIG. 7A and is obtained at a blood flow rate of 50 ml/min.
Figure 7B:
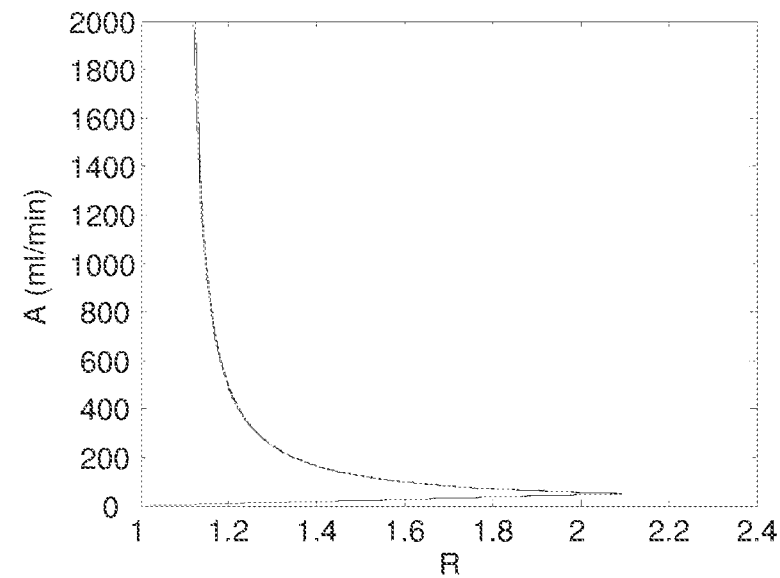
FIG. 7C illustrates determination of access flow rate using the current functions of FIGS. 7A-7B.

It has been found that it is possible to make the current function, as used in step 46, effectively independent of cardiac output CO and dialyzer parameter $k_0A$ by clever selection of control values in steps 41, 43. FIG. 7A shows ratio functions at control values [B=100 ml/min, D=500 ml/min], and for two different cardiac outputs CO=3 l/min and 9 l/min and two dialyzer parameter values $k_0A$=600 ml/min and 1600 ml/min. As seen, the ratio functions are essentially independent of CO and $k_0A$ for access flow rates below about 1000 ml/min. It is thus possible to use standard values for CO and $k_0A$ in the current function R=$f_c$(A, CO, $k_0A$). FIG. 7B is identical to FIG. 7A, but generated at control values [B=50 ml/min, D=500 ml/min]. Clearly, the ratio functions are independent of CO and $k_0A$ for all access flow rates. FIGS. 7A-7B also show that there is a turning point in the ratio functions at A=B. This means that there are two possible current values $A_m$ for each measured ratio $m_1$. However, the smaller $A_m$ is less likely to occur in clinical practice, since it would be noticed as an extremely low treatment efficiency. Thus, step 46 may be configured to automatically select the larger $A_m$.

Figure 7C:
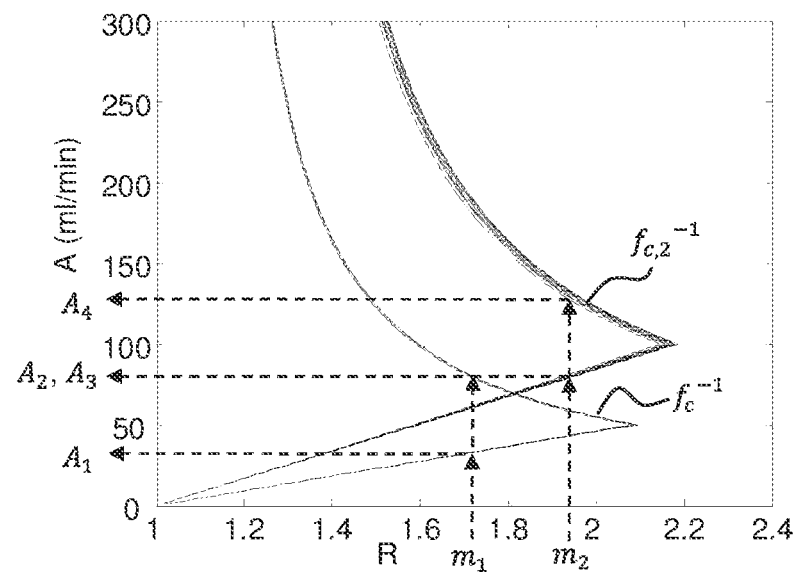

In a variant, the measurement phase 40 is designed to enable step 46 to evaluate the two possible current values for determination of $A_m$. This may be done by sequentially executing steps 41-45 for different settings of B and/or D. FIG. 7C is an enlarged view of a graph of the ratio functions in FIGS. 7A-7B. Assuming that steps 41-45 resulted in $m_1$=1.72 at B=50 ml/min and $m_2$=1.94 at B=100 ml/min, the dashed arrows at the respective current function $f_c^{-1}$, $f_{c,2}^{-1}$ indicate the possible values $A_1$=33 ml/min and $A_2$=80 ml/min for $m_1$, $A_3$=80 ml/min and $A_4$=130 ml/min for $m_2$. Step 46 may thus be configured to set $A_m$ based on the two most similar values among the possible values, e.g. by averaging. In the illustrated example, step 46 would set $A_m$=80 ml/min, based on $A_2$ and $A_3$. Step 46 may also indicate a computation error if the difference between the most similar values exceeds a predefined limit.

Figure 8:
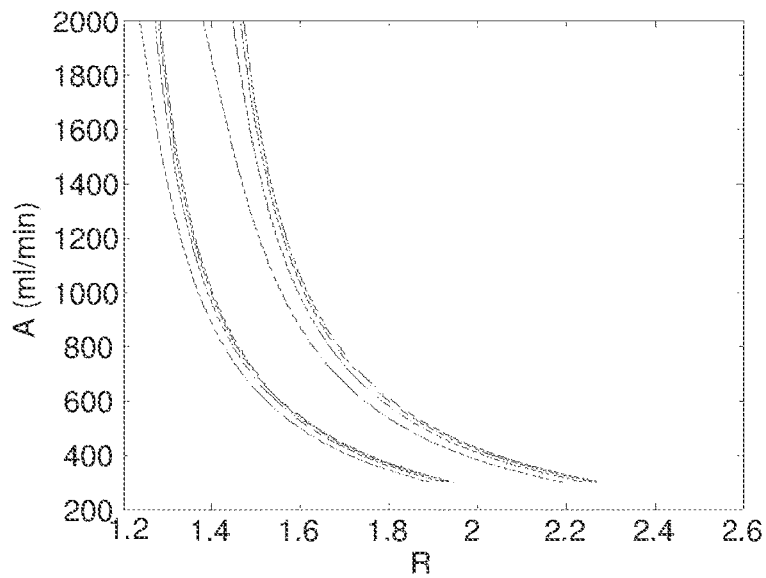
FIG. 8 is a plot of a current function obtained at a blood flow rate of 300 ml/min for various types of dialyzers and cardiac output values and a given measurement setting of the dialysis system in FIG. 3A.

By comparing FIG. 7A and FIG. 7B, it is seen that the range of ratios spanned by the current function for the more common access flow rates above 400 ml/min decreases with decreasing B. This means that the accuracy in the determination of access flow rate increases with increasing B. However, when B increases, so does the dependence on $k_0A$. FIG. 8 shows ratio functions at control values [B=300 ml/min, D=800 ml/min], and for two dialyzer parameter values $k_0A$=600 ml/min (left group of curves) and 1600 ml/min (right group of curves) and cardiac outputs CO=3, 5, 7 and 9 l/min. The leftmost curve in each group is for CO=3 l/min, which is quite low. This means that, in practice, standard values for CO may be used in the current function R=$f_c$(A, CO, $k_0A$). It is also seen that the slopes of the curves at high access flow rates are smaller than in FIGS. 7A-7B, which thus proves the above point that accuracy increases with B. To conclude, it may be beneficial to set, in steps 41 and 43, a blood flow rate B in excess of 100 ml/min, and preferably in excess of 150 or 200 ml/min to decrease the slope of the ratio function. However, to fully benefit from the increased accuracy obtained from the decreased slope, the dialyzer parameter $k_0A$ should be (approximately) known or measured.

Figure 9A:
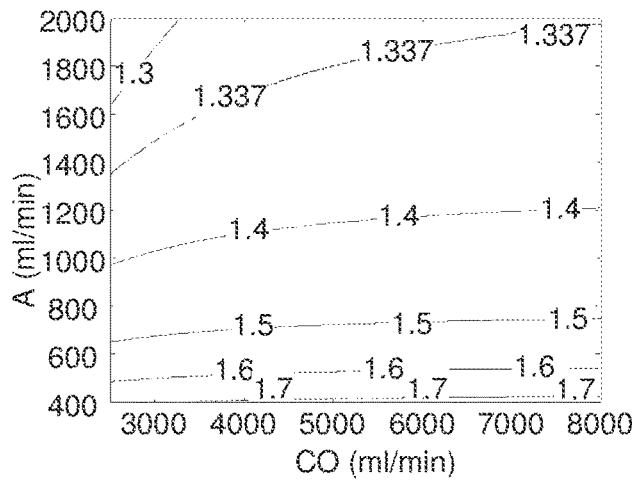
FIGS. 9A-9B are contour plots of current functions that relate efficiency ratio to access flow rate and cardiac output and are obtained for two different measurement settings of the dialysis system in FIG. 3A.
Figure 9B:
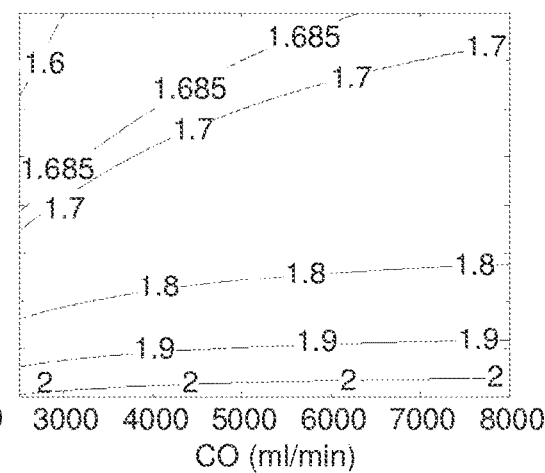
Figure 9C:
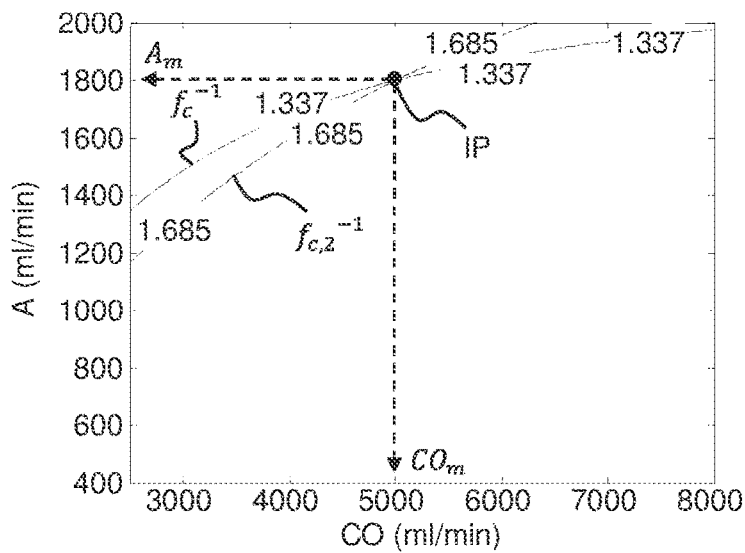
FIG. 9C illustrates determination of access flow rate and cardiac output based on a measured efficiency ratio and using the current functions of FIGS. 9A-9B.

If the actual value of $k_0A$ is (approximately) known or measured, it is possible to design the measurement phase 40 to enable step 46 to determine current values of access flow rate $A_m$ and cardiac output $CO_m$. This may be done by sequentially executing steps 41-45 for different settings of B and/or D. FIGS. 9A-9B are contour plots of a current function as a function of cardiac output CO and access flow rate A for a dialyzer with $k_0A$=1500 ml/min for two different sets of control values. FIG. 9A is obtained for control values [B=200 ml/min, D=800 ml/min], and FIG. 9B is obtained for control values [B=300 ml/min, D=200 ml/min]. The labels on the curves are values of the efficiency ratio R, and the curves show possible combinations of CO and A for these ratio values. Assuming that steps 41-45 resulted in $m_1$=1.337 for control values corresponding to the current function in FIG. 9A, and $m_2$=1.685 for control values corresponding to the current function in FIG. 9B, these values of $m_1$ and $m_2$ define a respective curve in CO, A space, as shown in FIG. 9C. Thus, step 46 may identify an intersection point IP between these curves (given by a first current function ($m_1$=$f_c^{-1}$) and a second current function ($m_2$=$f_{c,2}^{-1}$) in the CO, A space, where the coordinates of the intersection point IP give the current values $CO_m$, $A_m$, as indicated by dashed arrows in FIG. 9C.

Figure 10:
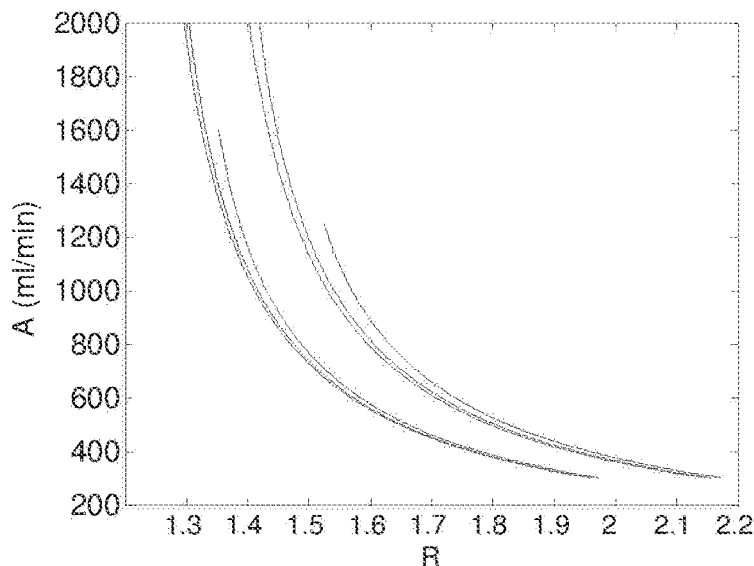
FIG. 10 is a plot of current functions that relate efficiency ratio to access flow rate and are obtained for two different in-vivo clearance values, various cardiac output values and a given measurement setting of the dialysis system in FIG. 3A.

If $k_0A$ is not known a priori, the measurement phase 40 may be designed to enable step 46 to use a measurement of the in-vivo clearance $K_{eff}$ during step 41 or step 43 to calculate a value of $k_0A$, which is then entered into the current function R=$f_c$(A, co, $k_0A$) for determination of $A_m$ based on $m_1$. The in-vivo clearance $K_{eff}$ may be estimated, measured or theoretically calculated using any known technique. In practice, the current function may thus be given as a function of $K_{eff}$ for one of the operating states instead of $k_0A$: R=$f_c$(A, CO, $K_{eff}$). It is understood that the above-described procedure for determining current values of access flow rate $A_m$ and cardiac output $CO_m$, based on $m_1$ and $m_2$, is equally applicable to such a ratio function. FIG. 10 shows ratio functions at control values [B=300 ml/min, D=800 ml/min], and for $K_{eff}$=235 ml/min (left group of curves) and 265 ml/min (right group of curves) and cardiac outputs CO=4, 6 and 8 l/min (from right to left in each group). As seen, it is possible to determine access flow rates up to about 1500 ml/min with reasonable accuracy.

Reversal of Treatment Fluid Flow

In the second embodiment with reversal of treatment fluid flow, the connections to the vascular access 3 are unchanged while the flow direction status of the dialyzer 4 is switched between counter-current and co-current. The measurement phase 40 in FIG. 4 may be performed with the flow direction status at the vascular access 3 being either normal or reversed. It can be shown that if the flow direction status is normal, a reversal of the treatment fluid direction will only change K in Eq. (14), from K according to Eq. (1) to K according to Eq. (3). Since Eq. (14) depends on CO-A, rather than CO and A separately, the current function becomes R=$f_c$(CO-A, $k_0A$) and step 46 is limited to determining CO-A. The parameter CO-A may be of interest, since it represents the part of the cardiac output that goes to the rest of the body. On the other hand, if the access devices 2', 2" are in the reversed position, a switch of flow direction of the treatment fluid will change K in Eq. (16), in which A and CO-A enter separately. Thus, the current function becomes R=$f_c$(A, CO, $k_0A$). Therefore, in the second embodiment with reversal of treatment fluid flow, it is preferable that both of the first and second operating states involve a flow direction status that is reversed at the vascular access 3. During the measurement phase 40, the flow direction status at the dialyzer 4 is switched from counter-current to co-current, or vice versa. The following examples presume that the first operating state involves a flow direction status that is counter-current at the dialyzer 4 and reversed at the vascular access 3.

Figure 11:
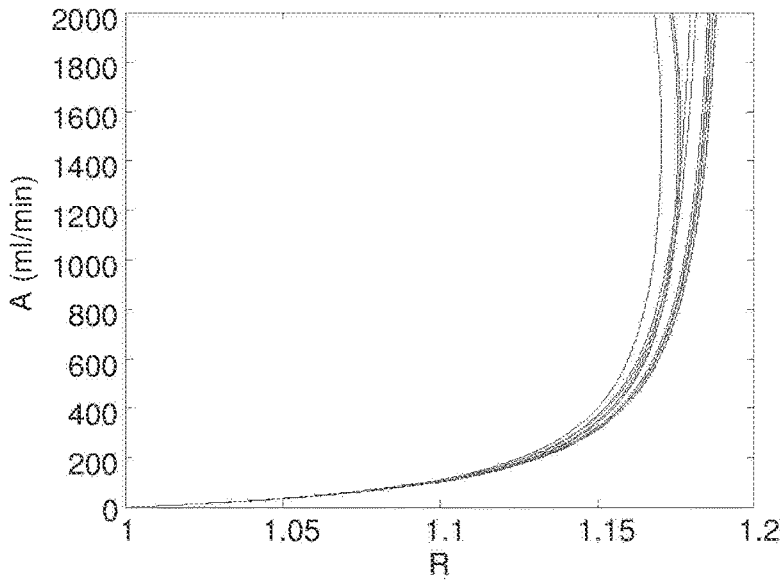
FIG. 11 corresponds to FIG. 7A and illustrates the current functions obtained for the same measurement setting of the dialysis system in FIG. 3B.

Like for the first embodiment, the dependence on $k_0A$ may be decreased or effectively eliminated by decreasing the blood flow rate B. FIG. 11 shows ratio functions that correspond to the ratio functions in FIG. 7A, i.e. for a blood flow rate B=100 ml/min. By comparing FIG. 11 with FIG. 7A, it is seen that the change in ratio is considerably smaller in FIG. 11, which will negatively affect the accuracy of the access flow value. Further, the dependence on $k_0A$ and CO is larger in FIG. 11. However, it may still be possible to use standard values of $k_0A$ and CO, by setting a blood flow rate B of 100 ml/min or less in steps 41 and 43.

Figure 12:
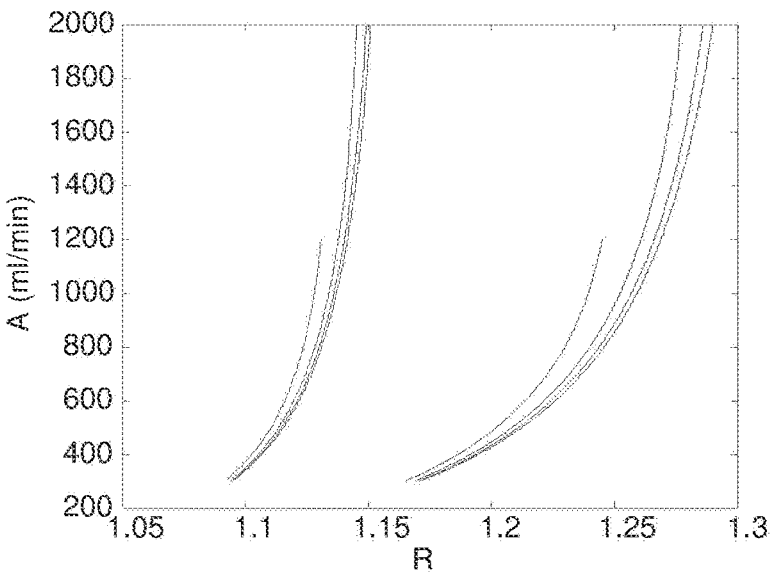
FIG. 12 corresponds to FIG. 8 and illustrates the current functions obtained for the same measurement setting of the dialysis system in FIG. 3B.

Like for the first embodiment, it can be shown that the range of ratios spanned by the current function for the more common access flow rates above 400 ml/min increases with increasing B, leading to an improved accuracy in the determination of access flow rate. However, increasing B leads to an increased dependence on $k_0A$. Thus, like for the first embodiment, it is preferable that the dialyzer parameter $k_0A$ is (approximately) known or measured and used in the current function $R=f_c(A, CO, k_0A)$. FIG. 12 corresponds to FIG. 8 and thus shows ratio functions at control values [B=300 ml/min, D=800 ml/min], and for two dialyzer parameter values $k_0A$=600 ml/min (right group of curves) and 1600 ml/min (left group of curves) and cardiac outputs CO=3, 5, 7 and 9 l/min (from left to right in each group of curves). As seen, the slope of the curves decrease with decreasing $k_0A$, which means that the accuracy of the current value $A_m$ determined by step 46 is better for dialyzers with small $k_0A$. Further, FIG. 12 also shows some dependence on cardiac output, which may be ignored or handled by implementing the measurement phase 40 with two executions of steps 41-45, in complete analogy with the measurement phase 40 described in relation to FIGS. 9A-9C, to determine current values of $A_m$, $CO_m$. Further, like for the first embodiment, knowledge of $k_0A$ may be replaced with a measurement of in-vivo clearance $K_{eff}$, resulting in the current function $R=f_c(A, CO, K_{eff})$.

Compared to the second embodiment, the first embodiment has the advantage that the measurement phase 40 may be performed with the access device 2', 2" in the normal position, i.e. the position used during blood treatment. As noted above, the second embodiment requires the access device 2', 2" to be placed in the reversed position before the measurement phase 40. The second embodiment, like the first embodiment, has the advantage that the entire measurement phase 40 may be implemented without manual intervention, and without the need of a specialized bloodline set or cassette. An advantage of the second embodiment over the first embodiment, is that the current function does not include a turning point that introduces a potential ambiguity when A<B. Further, the flow rate D of treatment fluid is automatically controlled by most TF circuits 1a irrespective of flow direction. Thus, the second embodiment is likely to provide well-controlled flow rates of both blood and treatment fluid. In the first embodiment, the blood flow rate B generated by the blood pump 5 may differ slightly between the pumping directions, even if the speed of the blood pump 5 is maintained invariant, since the switch of pumping direction may change the fluid pressure at the inlet of the pump 5. This may introduce slight inaccuracies to the current value $A_m$ determined in step 46. However, differences in blood flow rate B between the pumping directions may be reduced, if deemed necessary, by implementing well-known compensation techniques, e.g. as disclosed in U.S. Pat. No. 4,468,219, which adjust the speed of the pump based on measured fluid pressure upstream of the pump. Thus, in the context of FIG. 3A, the controller 15, or a dedicated pump controller (not shown), may be configured to adjust the control signal C2 for the blood pump 5 based on a pressure signal from a pressure sensor (not shown) located in the EC circuit 1a upstream of the blood pump 5 in the first or second operating state, so that the control signal C2 causes the blood pump 5 to maintain an essentially unchanged blood flow rate B in the first and second operating states. It is also conceivable to apply the compensation technique based on pressure signals from pressure sensors on both sides of the blood pump 5.

The controller 15 as described herein may be implemented by special-purpose software (or firmware) run on one or more general-purpose or special-purpose computing devices. In this context, it is to be understood that an "element" or "means" of such a computing device refers to a conceptual equivalent of a method step; there is not always a one-to-one correspondence between elements/means and particular pieces of hardware or software routines. One piece of hardware sometimes comprises different means/elements. For example, a processor serves as one element/means when executing one instruction, but serves as another element/means when executing another instruction. In addition, one element/means may be implemented by one instruction in some cases, but by a plurality of instructions in some other cases. Such a software controlled computing device may include one or more processors (cf. 17 in FIGS. 3A-3B), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The controller 15 may further include a system memory and a system bus that couples various system components including the system memory (cf. 18 in FIGS. 3A-3B) to the processor. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The controller 15 may include one or more communication interfaces, such as a serial interface, a parallel interface, a USB interface, a wireless interface, a network adapter, etc, as well as one or more data acquisition devices, such as an A/D converter. The special-purpose software may be provided to the controller 15 on any suitable computer-readable medium, transitory or non-transitory, including a record medium or a read-only memory. It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art. It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the machine 1 may be switched between the first and second operating states by manual intervention, instead of by a control signal. In one implementation, the controller 15 may instruct the operator, via the UI device 16 and before step 43, to manually execute a reversal of the blood pump 5 or switch the FSD 9. Even if the foregoing embodiments give the controller 15 the ability to set the measured property of the treatment fluid, by the control signal C4, the measurement phase 40 may be implemented also for embodiments that lack this ability, e.g. if the source 6 is configured to supply a ready-made treatment fluid of predefined composition.

In a variant of the embodiment in FIG. 3B, the FSD 9 is arranged in the EC circuit 1a, intermediate the dialyzer 4 and the blood pump 5. In this variant, the direction of the blood flow in the dialyzer 4 is switched between the first and second operating states. The foregoing discussion about the second embodiment with reversal of treatment fluid flow is equally applicable to this variant. The variant provides an alternative to prior art techniques, but the placement of the FSD 9 in the EC circuit 1a may call for a specialized bloodline set or cassette.

A further variant corresponds to a combination of FIGS. 3A-3B, i.e. the machine 1 comprises both the FSD 9 in the TF circuit 1b and the reversible blood pump 5 in the EC circuit 1a. Different implementations of the measurement phase 40 are conceivable in such a machine. In a first implementation, both the FSD 9 and the blood pump 5 are switched between the first and second operating states, reversing the flow direction of both blood and treatment fluid in the dialyzer 4 and also reversing the flow direction of blood at the vascular access 3. Thereby, the flow direction status at the vascular access 3 is changed between the first and second operating states, whereas the flow direction status at the dialyzer 4 in unchanged. Thus, the first implementation effectively produces the same flow reversal as the prior art techniques described in the Background section, which means that the access flow rate may be computed by any of the algebraic equations mentioned in the Background section. It should be noted that the first implementation, in contrast to the prior art techniques, achieves the flow reversal without the need for a specialized bloodline set or cassette in the EC circuit 1a. In a second implementation, the measurement phase 40 involves switching the machine between at least three operating states, by sequentially switching the FSD 9 and reversing the blood pump 5. Thus, the above-mentioned first and second operating states are supplemented by a third operating state. Thereby, it is possible to compute a first efficiency ratio (step 46 in FIG. 4) for the switch between the first and second operating states, and a second efficiency ratio for the switch between the second (or first) operating state and the third operating state. Since each of the first and second efficiency ratios are given by a respective current function, the second implementation generally makes it possible to compute further current values of the access flow rate or to compute a current value of another parameter. For example, the second efficiency ratio may be used as $m_2$ in the computations described above with reference to FIGS. 7C and 9C.

As noted hereinabove, one motivation for using the efficiency ratio R is to obtain a governing function $f_3$ that is independent of $(\alpha \cdot C_v - C_{d1})$, which generally is unknown. As seen from Eq. (17), this is may be achieved without taking a ratio of efficiency parameter values, if in-vivo clearance $K_{eff}$ is used as efficiency parameter. Thus, if the in-vivo clearance $K_{eff}$ is obtained for the first and second operating states (in steps 42, 44 of FIG. 4), the comparison parameter (in step 45 of FIG. 4) may be given by a difference of in-vivo clearance $K_{eff}$ between the first and second states, or a function thereof. Such a comparison parameter is an "efficiency difference" $\Delta K$. It is realized that the governing function for the efficiency difference $\Delta K$ is obtained by subtracting two functions given by Eq. (14) and/or (16), with K according to either Eq. (1) or (3), depending on flow direction status in the first and second operating states, respectively. Thus, the governing function $f_3$ may still be given in the format $\Delta K = f_3(A, CO, k_0A, D, B)$. It should be understood that all techniques described herein for determining access flow rate based on efficiency ratio R are equally applicable for determining access flow rate based on efficiency difference $\Delta K$.

The invention claimed is:

1. A device for determining a fluid flow rate in a vascular access of a patient when connected to a blood treatment machine, said blood treatment machine comprising an extracorporeal blood flow circuit with first and second access devices for connection to the vascular access and having a blood pump operable to generate a flow of blood in the extracorporeal blood flow circuit from the first access device through a blood compartment of a dialyzer and to the second access device, and a treatment fluid flow circuit configured to generate a flow of treatment fluid through a treatment fluid compartment of the dialyzer, said treatment fluid compartment being separated from the blood compartment by a semi-permeable membrane, said device being configured to, during a measurement phase:
cause the blood treatment machine to switch between a first operating state and a second operating state, wherein the second operating state differs from the first operating state at least by a change of flow direction of the blood or the treatment fluid through the dialyzer;
acquire an output signal of at least one sensor in the blood treatment machine in the first and second operating states;
compute, based on the output signal, a measurement value of a comparison parameter that compares treatment efficiency in the first operating state to treatment efficiency in the second operating state;
obtain, for first and second sets of control values of operating parameters of the blood treatment machine in the first and second operating states, a current function that relates the comparison parameter to the fluid flow rate in the vascular access, the operating parameters including a cardiac output of the patient, a characteristic parameter of the dialyzer, a flow rate of the treatment fluid through the dialyzer, and a flow rate of the blood through the dialyzer; and
determine, based on the measurement value, an estimated value of the fluid flow rate in the vascular access so that the current function yields the measurement value.

2. The device of claim 1, which is configured to cause a reversal of a pumping direction of the blood pump between the first and second operating states, so as to change the flow direction of the blood through the blood compartment of the dialyzer between the first and second operating states.

3. The device of claim 1, which is configured to cause at least one flow switching device in the treatment fluid flow circuit to change the flow direction of the treatment fluid through the treatment fluid compartment of the dialyzer between the first and second operating states.

4. The device of claim 3, wherein, during the measurement phase, the first and second access devices are connected to upstream and downstream portions, respectively, of the vascular access.

5. The device of claim 1, which is configured to, between the first and second operating states, cause at least one flow switching device in the treatment fluid flow circuit to change the flow direction of treatment fluid through the treatment fluid compartment of the dialyzer and cause the blood pump to reverse its pumping direction so as to change the flow direction of blood through the blood compartment of the dialyzer and the flow direction of blood through the first and second access devices.

6. The device of claim 1, which is configured to compute the measurement value of the comparison parameter to represent one of: a ratio of the treatment efficiencies in the first and second operating states, and a difference between the treatment efficiencies in the first and second operating states.

7. The device of claim 1, which is further configured to cause, by a first control signal, the treatment fluid flow circuit to generate an essentially fixed value of a fluid property of the treatment fluid that enters the dialyzer during the first and second operating states, said fluid property being measured by the at least one sensor.

8. The device of claim 7, which is configured to maintain, between the first and second operating states, the essentially fixed value of the fluid property.

9. The device of claim 8, which is further configured to, based on the output signal, compute a first difference in the fluid property between an inlet and an outlet of the treatment fluid compartment in the first operating state, and a second difference in the fluid property between the inlet and the outlet of the treatment fluid compartment in the second operating state, and wherein the device is configured to compute the measurement value as a function of a quotient of the first and second differences.

10. The device of claim 9, which is further configured to, in advance of the measurement phase, compute at least one of the first and second differences and, if said at least one of the first and second differences is lower than a predefined minimum value, control a source of treatment fluid in the treatment fluid flow circuit to adjust the fluid property of the treatment fluid so that said at least one of the first and second differences exceeds the predefined minimum value.

11. The device of claim 7, wherein the fluid property is a physical and/or chemical property of the treatment fluid.

12. The device of claim 7, wherein the fluid property is one of a temperature, an electrical conductivity, and a concentration of a substance that is present in the blood and is capable of exchanging across the semi-permeable membrane.

13. The device of claim 1, which is further configured to obtain dedicated settings for the blood pump and the treatment fluid flow circuit and apply the dedicated settings to cause, by a first control signal, the treatment fluid flow circuit to generate a fixed flow rate of treatment fluid through the dialyzer during the first and second operating states, and to cause, by a second control signal, the blood pump to generate an essentially fixed flow rate of blood through the dialyzer during the first and second operating states.

14. The device of claim 1, which is further configured to obtain, from an electronic memory, the current function among a set of predefined functions based on the first and second sets of control values.

15. The device of claim 1, which is further configured to obtain a governing function from an electronic memory, and generate the current function by entering at least part of the first and second sets of control values into the governing function.

16. The device of claim 1, wherein the current function is given by an algebraic function, or a numerical inverse thereof, wherein the algebraic function has the comparison parameter as output variable and the access flow rate as input variable and is derived for a hydraulic model of the blood treatment machine as connected to the patient and given a current flow direction of blood and treatment fluid through the dialyzer and a current flow direction of blood to the first and second access devices.

17. The device of claim 1, wherein the first and second sets of control values comprise a flow rate of blood through the dialyzer in the first and second operating states, a flow rate of treatment fluid through the dialyzer in the first and second operating states, and one of a mass transfer area coefficient of the dialyzer and an in-vivo clearance of the blood treatment machine in one of the first and second operating states.

18. The device of claim 17, wherein the current function is obtained for a generic value of cardiac output of the patient.

19. The device of claim 17, which is configured to set the flow rate of blood through the dialyzer equal to or less than 100 ml/min, and preferably equal to or less than 50 ml/min, in the first and second operating states, and wherein the control value for the mass transfer area coefficient is a generic value.

20. The device of claim 19, which is further configured to cause the blood treatment machine to perform a second switch between the first and second operating states while applying third and fourth sets of control values which differ from the first and second sets of control values by at least the flow rate of blood through the dialyzer, acquire the output signal of the at least one sensor in the first and second operating states, and compute a second measurement value of the comparison parameter, wherein the device is configured to determine two candidate values of the fluid flow rate for each of the measurement value and the second measurement value, and determine the estimated value of the fluid flow rate based on the candidate values, preferably the two most similar candidate values.

21. The device of claim 17, which is configured to set the flow rate of blood through the dialyzer to exceed 100 ml/min in the first and second operating states, and wherein the control value for the mass transfer area coefficient is a specific value for the dialyzer.

22. The device of claim 21, wherein the current function relates the comparison parameter to the fluid flow rate and cardiac output of the patient, and wherein the device is further configured to cause the blood treatment machine to perform a second switch between the first and second operating states while applying third and fourth sets of control values of the operating parameters, acquire the output signal of the at least one sensor in the first and second operating states, compute a second measurement value of the comparison parameter, obtain a second current function that relates the comparison parameter to the fluid flow rate and the cardiac output for the third and fourth sets of control values, and determine the estimated value of the fluid flow rate, and optionally an estimated value of the cardiac output, based on the current function set to yield the measurement value and the second current function set to yield the second measurement value.

23. The device of claim 22, which is configured to determine the estimated value of the fluid flow rate, and optionally the estimated value of the cardiac output, by identifying an intersection between the current function and the second current function in a two-dimensional space defined by the fluid flow rate in the vascular access and the cardiac output.

24. The device of claim 1, wherein said at least one sensor is one of a concentration sensor, a temperature sensor, a conductivity sensor, an optical absorbance sensor, a polarimetry sensor and a density sensor.

25. A blood treatment machine, comprising:
- an extracorporeal blood flow circuit with first and second access devices for connection to a vascular access of a patient and having a blood pump operable to generate a flow of blood from the first access device through a blood compartment of a dialyzer and to the second access device;
- a treatment fluid flow circuit configured to generate a flow of treatment fluid through a treatment fluid compartment of the dialyzer, said treatment fluid compartment being separated from the blood compartment by a semi-permeable membrane; and
- the device according to claim 1.

* * * * *